(12) United States Patent
Lee et al.

(10) Patent No.: US 8,149,397 B2
(45) Date of Patent: Apr. 3, 2012

(54) METALLIC NANOSTRUCTURES ADAPTED FOR ELECTROMAGNETIC FIELD ENHANCEMENT

(75) Inventors: Luke P. Lee, Orinda, CA (US); Yu Lu, Riverside, CA (US); Gang L. Liu, Berkeley, CA (US); Jaeyoun Kim, Ames, IA (US)

(73) Assignee: The Regents of the University of California, Oakland, CA (US)

( * ) Notice: Subject to any disclaimer, the term of this patent is extended or adjusted under 35 U.S.C. 154(b) by 448 days.

(21) Appl. No.: 11/886,390

(22) PCT Filed: Mar. 14, 2006

(86) PCT No.: PCT/US2006/009339
§ 371 (c)(1),
(2), (4) Date: Sep. 3, 2008

(87) PCT Pub. No.: WO2006/099494
PCT Pub. Date: Sep. 21, 2006

(65) Prior Publication Data
US 2009/0213369 A1    Aug. 27, 2009

Related U.S. Application Data

(60) Provisional application No. 60/661,774, filed on Mar. 14, 2005.

(51) Int. Cl.
*G01J 3/44* (2006.01)
(52) U.S. Cl. .................................................. 356/301
(58) Field of Classification Search .............. 356/301; 427/212; 252/587; 424/617; 422/99; 977/954
See application file for complete search history.

(56) References Cited

U.S. PATENT DOCUMENTS

| | | | |
|---|---|---|---|
| 5,023,139 A | 6/1991 | Birnboim et al. | |
| 5,133,764 A * | 7/1992 | Pappas et al. | 623/23.14 |
| 6,778,316 B2 | 8/2004 | Halas et al. | |
| 6,888,665 B2 | 5/2005 | Feldheim et al. | |
| 2005/0227063 A1* | 10/2005 | Lawandy | 428/323 |

OTHER PUBLICATIONS

Yu Lu et al. (Nanophotonic Crescent Moon Structures with Sharp Edge for Ultrasensitive Biomolecular Detection by Local Electromagnetic Field Enhancement Effect, American Chemical Society, 2004, vol. 5, No. 1, pp. 119-124).*
Gurley, Lynne A., Notification of Transmittal of the International Search Report and the Written Opinion of the International Searching Authority, or the Declaration, International Search Report, Written Opinion, Mar. 5, 2008.
Nickitas-Etienne, Athina, International Preliminary Report on Patentability and Written Opinion, Date of Issuance of Report: Mar. 10, 2009, International Application No: PCT/US06/09339.

* cited by examiner

*Primary Examiner* — Tarifur Chowdhury
*Assistant Examiner* — Abdullahi Nur
(74) *Attorney, Agent, or Firm* — Joseph R. Baker, Jr.; Gavrilovich, Dodd & Lindsey LLP

(57) ABSTRACT

The disclosure relates to metallic nanophotonic crescent structures, or "nanocrescent SERS probes," that enhance detectable signals to facilitate molecular detections. More particularly, the nanocrescent SERS probes of the disclosure possess specialized geometries, including an edge surrounding the opening that is capable of enhancing local electromagnetic fields. Nanosystems utilizing such structures are particularly useful in the medical field for detecting rare molecular targets, biomolecular cellular imaging, and in molecular medicine.

19 Claims, 21 Drawing Sheets

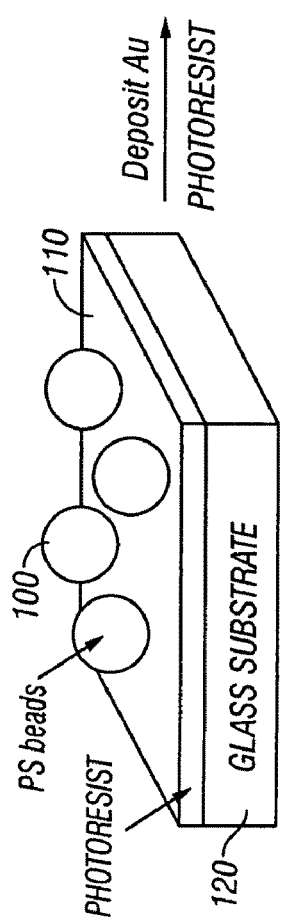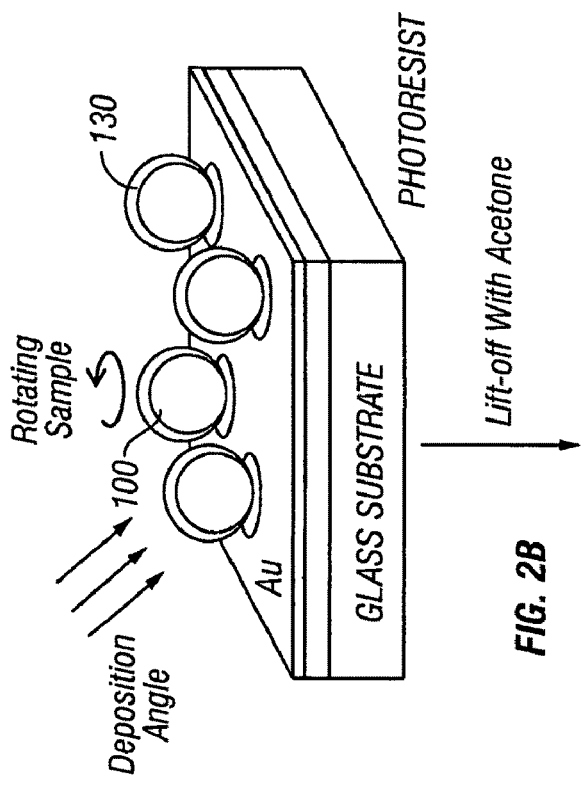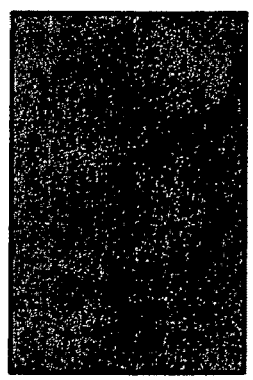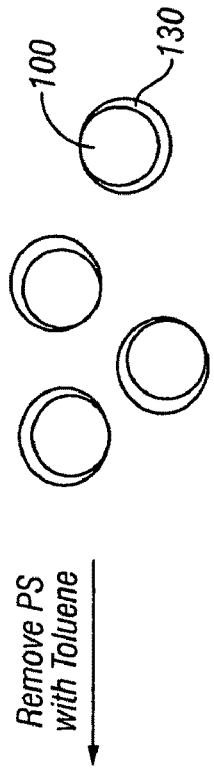
FIG. 2A
FIG. 2B
FIG. 2C
FIG. 2D

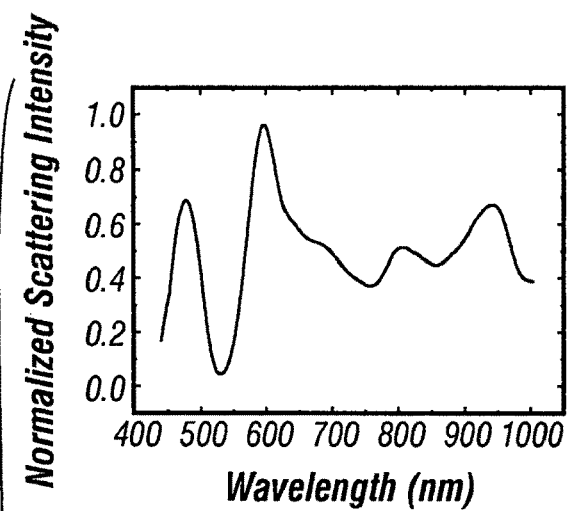
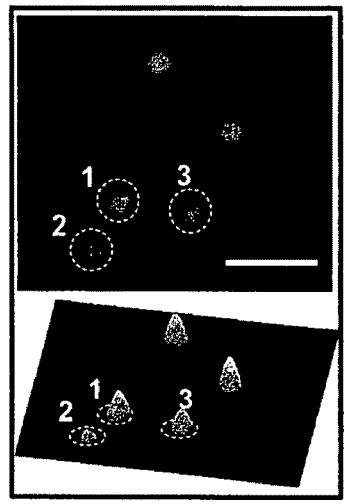
FIG. 4A
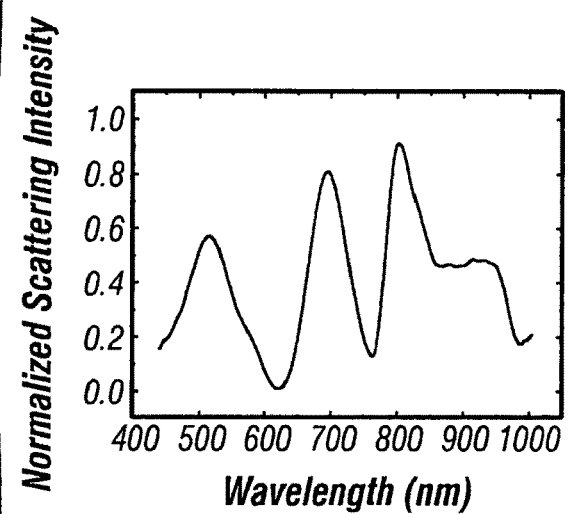
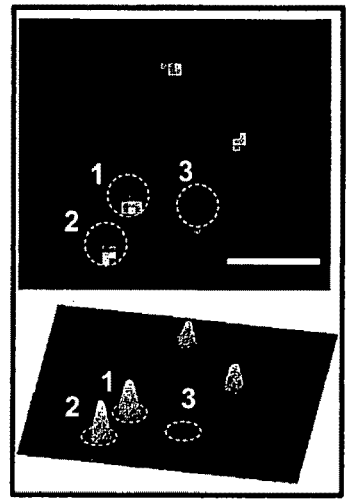
FIG. 4D
FIG. 4B
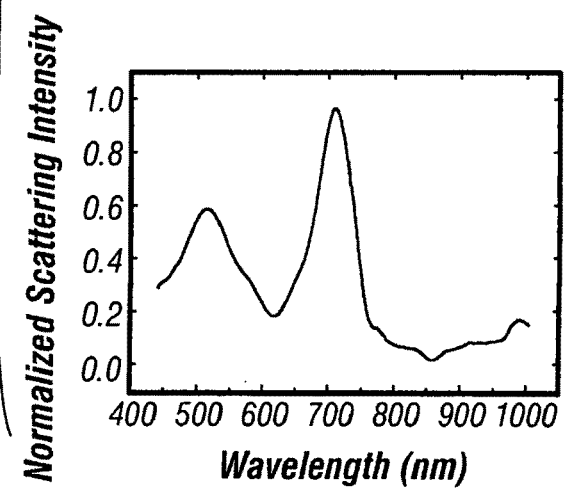
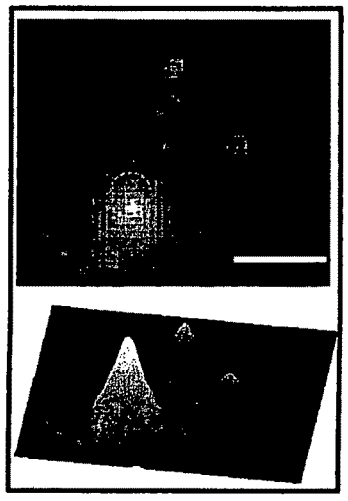
FIG. 4C Functional Group Au Ag Magnetic Thin Film (Fe)

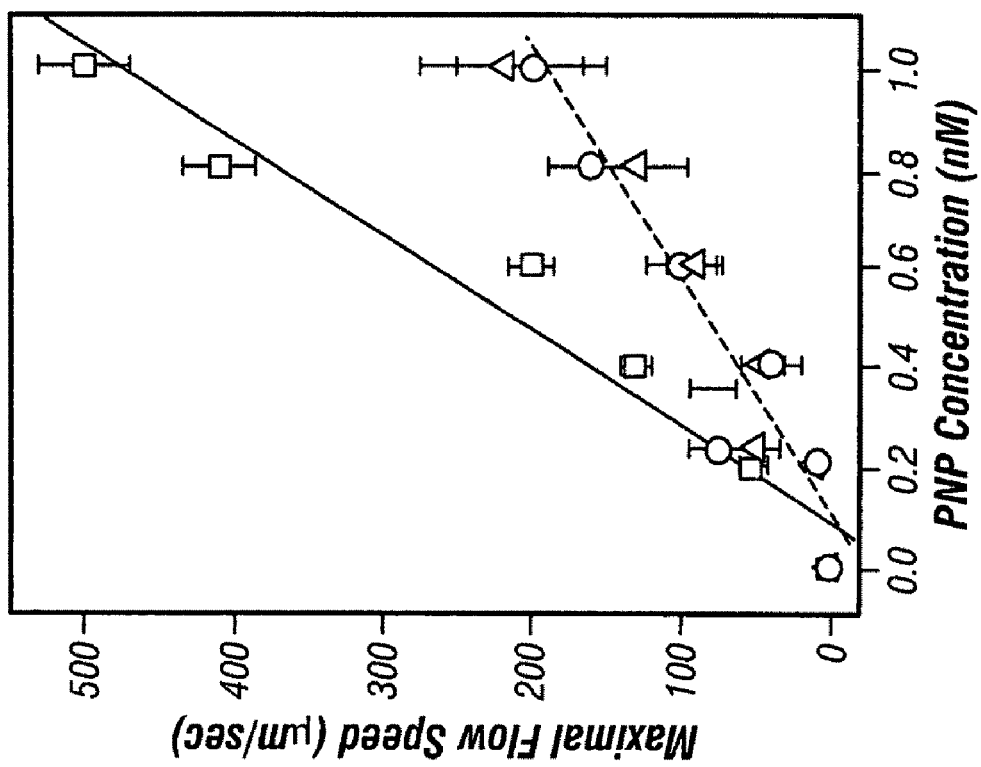
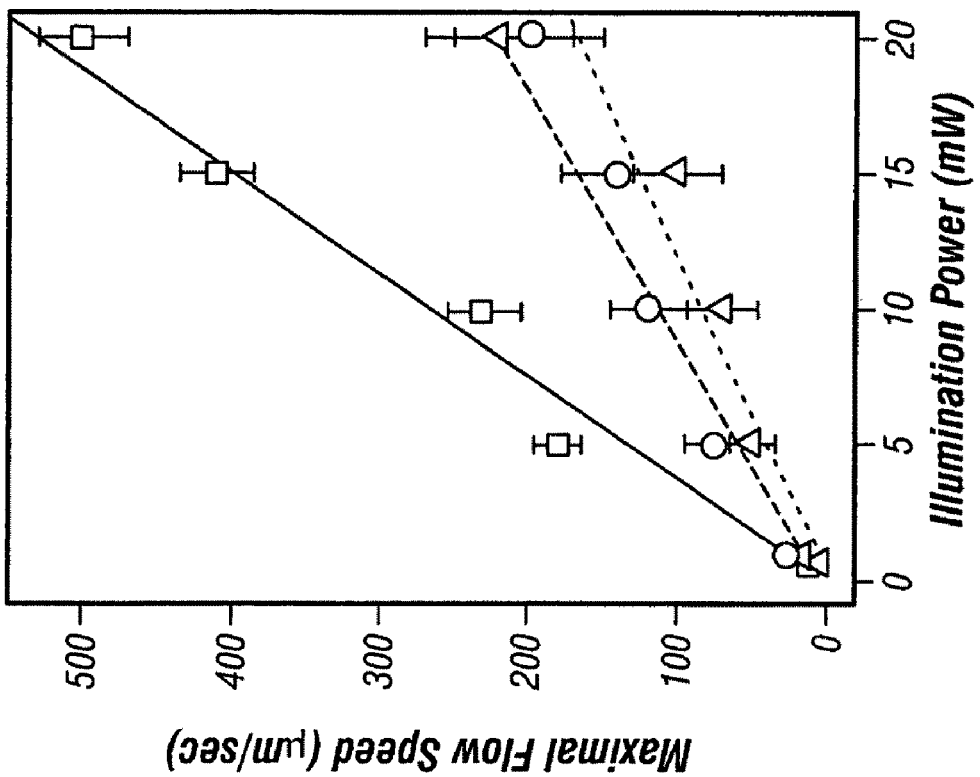
FIG. 11B
FIG. 11A

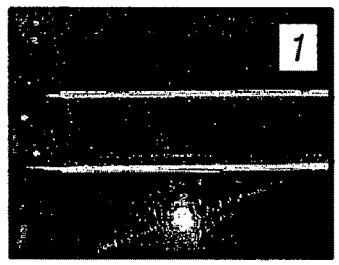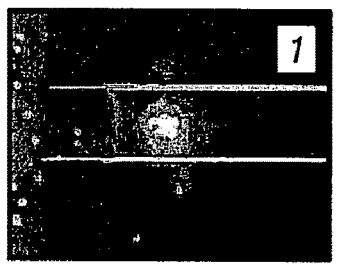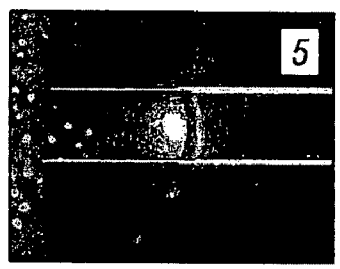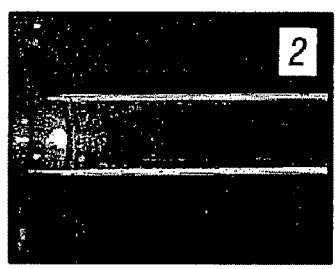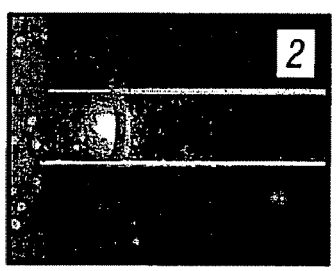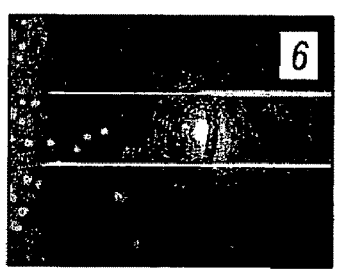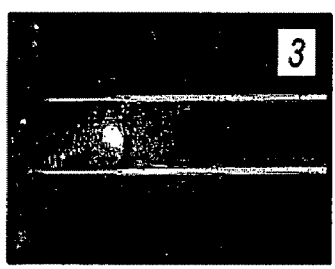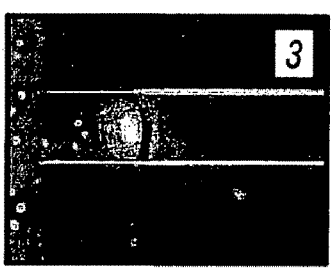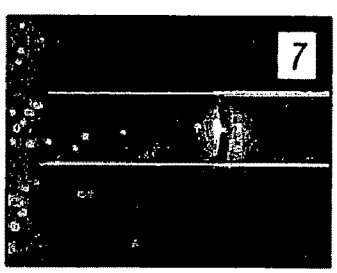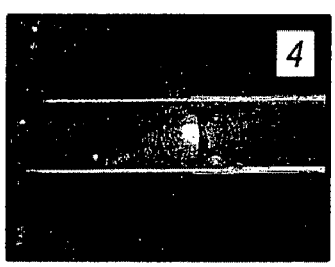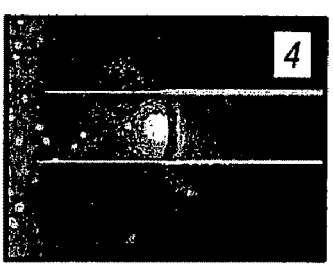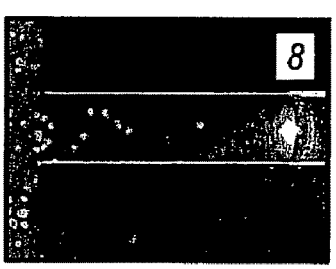
*FIG. 13A*            *FIG. 13B*

METALLIC NANOSTRUCTURES ADAPTED FOR ELECTROMAGNETIC FIELD ENHANCEMENT

CROSS-REFERENCE TO RELATED APPLICATIONS

This application claims priority under 35 U.S.C. §119 to U.S. Provisional Application Ser. No. 60/661,774, filed Mar. 14, 2005, and to International Application No. PCT/US06/009339, filed Mar. 14, 2006, the disclosures of which are incorporated herein by reference.

STATEMENT REGARDING FEDERAL SPONSORED RESEARCH

The U.S. Government has certain rights in this invention pursuant to Grant No. EEC-9813302 by the National Science Foundation.

FIELD OF THE INVENTION

The disclosure relates to nanostructures that enhance detectable signals to facilitate molecular detections and molecular imaging. More particularly, the nanostructures of the disclosure possess geometries capable of enhancing local electromagnetic fields. Nanosystems utilizing such structures are particularly useful in the medical field for detecting rare molecular targets, biomolecular cellular imaging, drug delivery and in molecular medicine.

BACKGROUND

Raman spectroscopy is a label-free technique desired for biomolecular detections and molecular dynamic study. Surface enhanced Raman scattering (SERS) improves the sensitivity by amplifying the original Raman scattering intensity for several or even tens of orders of magnitude. Spherical gold and silver nanoparticles have been reported as substrates in SERS-based molecule detections due to their advantages in local scattering field enhancing, surface chemical modifications, biocompatibility, and well-established chemical synthesis process. The intrinsic plasmon resonance of single nanospheres and the plasmon coupling between adjacent nanospheres are considered as a key and necessary condition for local field enhancing. The optimal SERS substrate of spherical nanoparticle assemblies depends on the size, the local dielectric environment and the interparticle distance.

Surface-enhanced Raman scattering (SERS) spectroscopy shows chemical-bond information, and is one of the best methods for label-free biomolecular imaging. Conventional SERS substrates require multiple plasmonic couplings via many colloidal nanoparticles requiring particular coupling distances that are difficult to control in solution or biomolecular environments. In conventional chemical synthesis or batch fabrications, the interparticle distance is difficult to control due to the stochastic distribution of the nanospheres on a substrate.

The nanosphere is used because of its unique, highly desirable properties that make it a superior detection platform for life science research, in vitro diagnostic testing, and in vivo imaging. Other structures such as nanotips and nanorings have also been demonstrated for use in high resolution SERS spectroscopy and imaging. These structures provide significant field enhancement in experiments and in simulations but they have proved to be difficult to fabricate consistently. Although nanostructures for use in Raman Spectroscopy have been developed, there continues to be a need to develop nanostructures that have improved detect ability and ease of fabrication.

SUMMARY OF THE INVENTION

The invention provides a nanostructure that undergoes Surface enhanced Raman scattering (SERS) when contacted with electromagnetic radiation at near infrared wavelengths.

The invention also provides a metallic nanostructure comprising a spherical, asymmetrical tapered metallic shell having a single round opening surrounded by an edge, wherein the nanostructure has an inner radius r and an outer radius R, wherein said outer radius R is greater than the inner radius r, and wherein the nanostructure has a greatest thickness opposite the opening, and wherein the edge has a thickness that is less than the greatest thickness.

The invention further provides a method for making a nanostructure of the invention. The method includes dispersing template nanostructures on a surface; depositing one or more metal materials onto the template nanostructure to form coated nanostructures; and removing the coated nanostructures from the surface, wherein the surface of the template nanostructure in contact with the surface comprises less metal material than any other part of the template nanostructure. In one embodiment, the method includes decomposing the template nanostructure.

The invention also includes a pharmaceutical composition comprising a plurality of nanostructures of the invention in a pharmaceutically acceptable carrier.

In some embodiments of the invention, a nanostructure of the invention comprises a functional group that associates with a target analyte.

The invention includes a method for detection of a target analyte, comprising providing a plurality of nanostructures of the invention; a device that measures surface enhanced Raman spectroscopy (SERS) detection; contacting the plurality of nanostructures with a fluid suspected of or having the target analyte, contacting the fluid with an electromagnetic radiation at a desired wavelength sufficient to cause SERS; and detecting SERS from the plurality of nanostructures using the device.

The invention also includes a microfluidic system comprising one or more microfluidic channels; a fluid; a plurality of nanostructures of the invention, wherein the plurality of nanostructures are dispersed in the fluid; and means for contacting the leading edge of the fluid in the microchannel with electromagnetic radiation sufficient to induces surface enhanced Raman scattering (SERS), wherein the SERS moves the fluid through the microchannel.

Additional aspect of the invention will be understood from the description below, the attached drawings and the appended claims.

DESCRIPTION OF DRAWINGS

FIGS. 2A-D shows a fabrication procedure of gold nanocrescent SERS probes. (a) Casting a monolayer of spherical polystyrene colloids on a photoresist coated glass substrates. (b) Coating a gold layer on the surfaces of polystyrene colloids by electron beam evaporation or directional ion-beam deposition. The sample is kept rotating at a certain angle with respect to the gold target during deposition. The shape of the nanocrescent SERS probes depends on the deposition angle and the size of the polystyrene spheres. (c) Lift-off of the gold-coated polystyrene spheres from the substrate. (d) Scanning electron microscopy of gold nanocrescent SERS probes. The dissolution of the colloidal particles releases the nanocrescent SERS probes into a suspension. The nanocrescent SERS probes are then collect and placed on a substrate. For the convenience of demonstration in SEM, the shown nanocrescent SERS probes were not subject to dilution in water. The scale bar is 200 nm.

FIGS. 4A-D show scattering images and spectra of gold nanocrescent SERS probes. (a) True-color dark-field scattering image of gold nanocrescent SERS probes. The laser excitation is turned off and no optical filter is placed in the optical path when taking this image. (b) B/W dark-field scattering image of the same nanocrescent SERS probes at near infrared region (>797 nm). The laser excitation is still off while two 797 nm long-pass optical filters (optical density >6) are placed in the optical path when taking this image. (c) B/W dark-field scattering image of the same nanocrescent SERS probes with one nanocrescent SERS probe excited by laser. The two optical filters are used. The scale bar is 10 μm in all three images and the contrast of each image is scaled individually. (d) The dark-field scattering spectra of the three marked nanocrescent SERS probes.

FIGS. 11A-B shows the flow speed by optofluidic control. A) Maximal flow speed of 1 nM PNP water solution vs. the illumination optical power. The open square (□) circle (o) and triangle (Δ) correspond to the microchannels in the width of 10, 40 and 80 μm, respectively. The solid, dashed, and dotted lines represent the linear fits of the above three data sets, respectively. B) Flow speed vs. the PNP concentration for the optofluidic control with a 20 mW laser spot. The symbols and lines have the same representations as those in (A). The error bars in both plots represent the standard deviation of the 5 measurements for each data point.

FIGS. 13A-B shows the optofluidic transportation of Jurkat T-cells stained with Calcein AM fluorescence dye. A) Transportation of a single cell. B) Transportation of multiple cells. The depth and width of the channel are 50 μm and 100 μm, respectively. The interested cell is marked with red circles to elucidate the moving by optofluidic control. The fluorescence intensities of most transported cells remain same even when the cells are only tens of micrometers away from the photothermally hot area. A darkfield illumination is applied to visualize the microchannel boundaries and liquid flow.

DETAILED DESCRIPTION

Figure 1A:
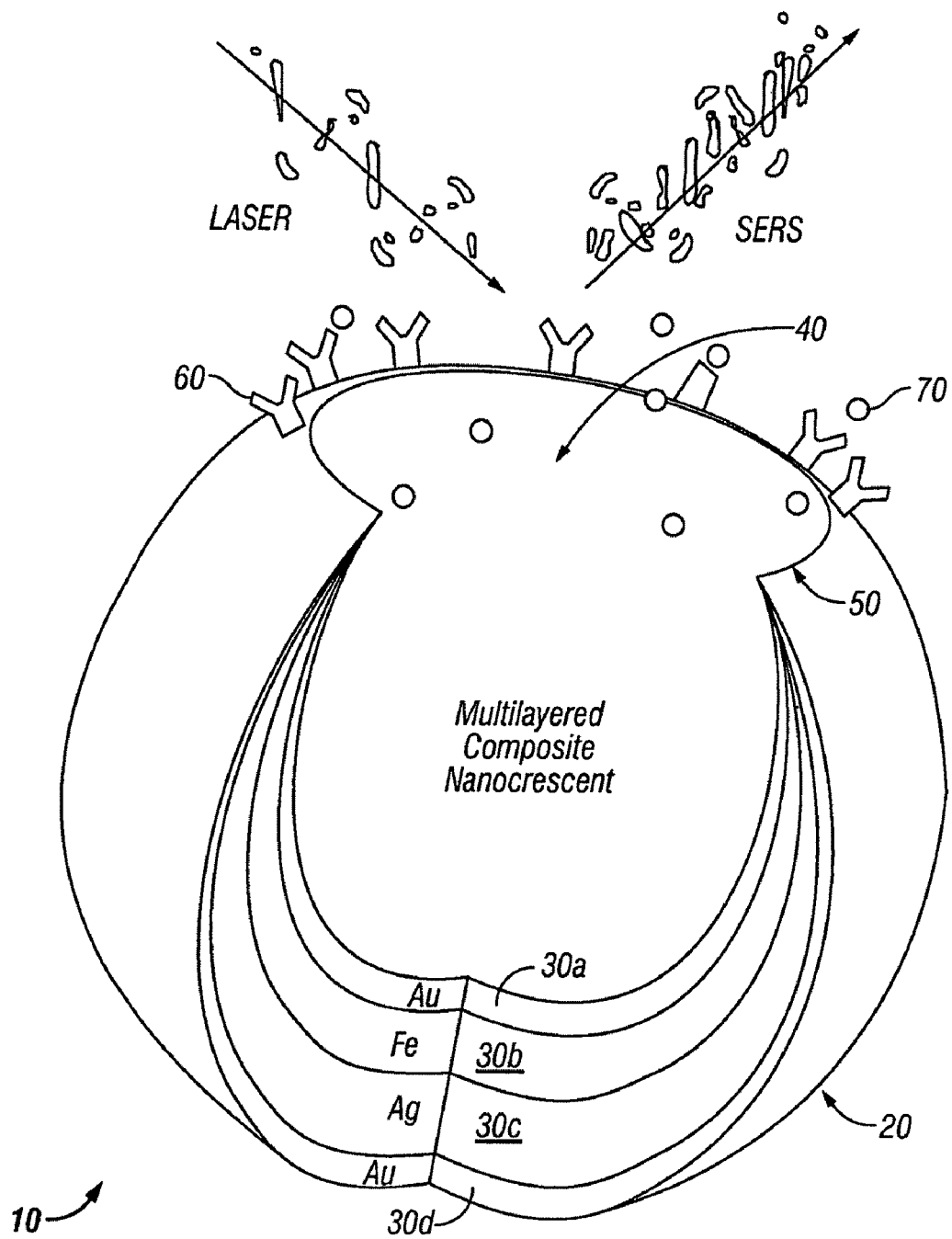
FIGS. 1A-E shows an example of a nanostructure of the invention. The figure depicts gold nanocrescent SERS probe structures with sharp edges. (a) Shows a general schematic of a nanostructure of the invention. (b) Conceptual schematics of a nanocrescent SERS structure. The gold surface can be functionalized with biomolecular linkers to recognize specific biomolecules. A sharp edge of the nanocrescent SERS probe structure can enhance the Raman scattering intensity so that the biomolecules on it can be detected. (c) Geometrical schematics of a nanocrescent SERS probe. A gold nanocrescent SERS probe with edges integrate the geometric functional features of nanoring and nanotips. (d) Transmission electron microscope images of nanocrescent SERS probes. Shown nanocrescent SERS probes are about 300 nm-inner diameter, 100 nm-bottom-thickness, but with different orientations. The scale bars are 100 nm. (e) Schematic diagram of a SERS imaging system and the magnetic manipulation system for intracellular biomolecular imaging (in fluids) using stand-alone magnetic nanocrescent SERS probes.
Figure 1B:
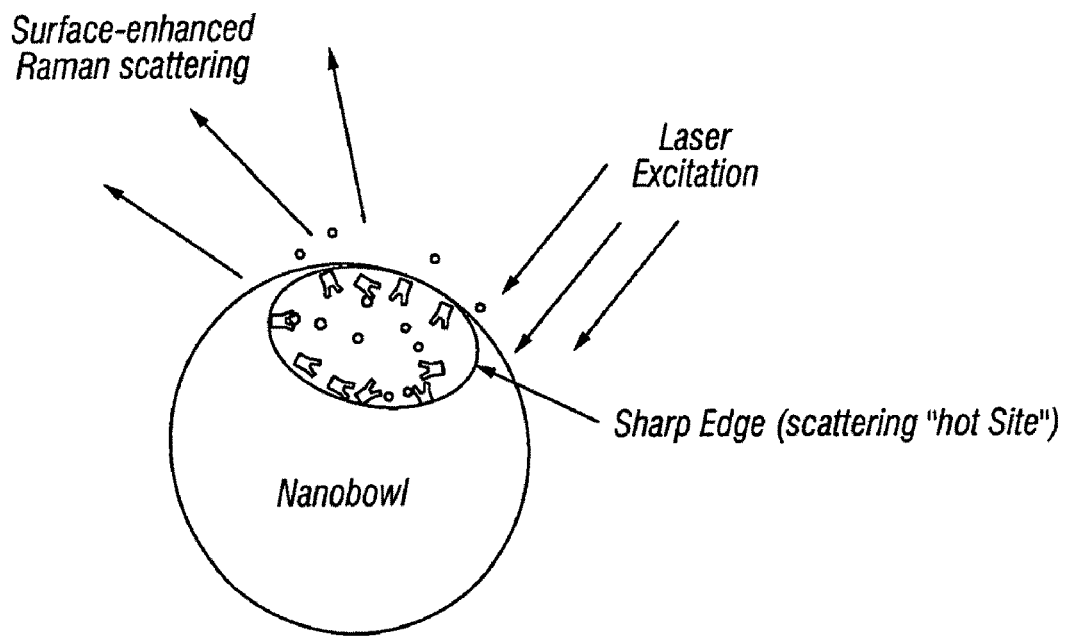

As used herein and in the appended claims, the singular forms "a," "and," and "the" include plural referents unless the context clearly dictates otherwise. Thus, for example, reference to "a nanoparticle" includes a plurality of such nanoparticle and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Techniques for label-free single molecular level detection and recognition of specific biomolecules are important in defense, medical, and environmental sensing applications. In this field, optical methods based on spectroscopy have been predominant owing to their non-destructive nature. Especially promising methods are label-free schemes such as Raman or extinction spectroscopy. Recently these spectroscopic techniques gain reinforced interests due to technical advances in metallic nandstructures. Under optical excitations of proper frequency, a metallic nanostructure sustains a plasmon resonance that results in highly enhanced local electromagnetic fields and distinct spectral extinction characteristics. For sensing applications, the field enhancement is utilized for surface-enhanced Raman spectroscopy (SERS) and the spectral extinction characteristics are used to detect the changes in local refractive index. The plasmon resonance characteristic depends strongly on the topology of each nanostructure. The shape of the nanostructures; however, has been limited to symmetric and/or particulate due to fabrication constraints.

Surface enhanced Raman spectroscopy (SERS) retains all of the advantages of normal Raman spectroscopy while achieving significantly stronger signal intensity. SERS is a process whereby the Raman scattering signal is increased when a Raman-active molecule is spatially confined within range of the electromagnetic fields generated upon excitation of the localized surface plasmon resonance of nanostructured metal surfaces. Both chemical and conformational information can be elucidated from SERS. Accordingly, SERS possesses many desirable characteristics as a tool for the chemical analysis of in vivo molecular species including high specificity, attomole to high zeptomole mass sensitivity, micromolar to picomolar concentration sensitivity, and interfacial generality (Smith and Rodger, In Handbook of Vibrational Spectroscopy; Chalmers, J. M., Griffiths, P. R. Eds.; John Wiley & Sons: Chichester, UK, 2002; Vol. 1 pp 775-784).

The signature of a noble metal nanostructure is the localized surface plasmon resonance. This resonance occurs when the correct wavelength of electromagnetic energy (e.g., light) strikes a noble metal nanostructure causing the plasma of conduction electrons to oscillate collectively. The resonance oscillation is localized near the surface region of the nanostructure. Such resonance is advantageous in that the nanostructure is selectively excited at a particular photon absorption, which results in the generation of locally enhanced or amplified electromagnetic fields at the nanostructure surface. The resonance for noble metal nanostructures (e.g., in the 20-500 nm range) occurs in the visible and IR regions of the spectrum and can be measured by UV-visible-IR extinction spectroscopy. The location of the resonance is related to the resulting SER spectrum.

Normal Raman scattering is a scattering process in which photons incident on a sample transfer energy to or from the sample's vibrational or rotational modes. Individual bands in a Raman spectrum are characteristic of specific molecular motions. As a result, each analyte has its own unique Raman signature. When a Raman-active molecule is positioned within an electromagnetic field generated upon excitation of the resonance of a nanostructure, the Raman signal increases by multiple folds of magnitude.

Raman imaging of living cells can nondestructively probe the intracellular biochemical dynamics without prior fluorescent or radioactive labeling, but the formidably low efficiency of Raman scattering hinders its applications in the detection of molecules at micromolar or lower concentrations. However, SERS by metallic nanostructures increases the original Raman scattering intensity many orders of magnitude, which makes the Raman detection of low concentration molecules practical.

Colloidal Au or Ag nanoparticle clusters are commonly used as SERS substrates, and Raman enhancement factors as high as $10^{14}$ have been reported in single-molecular-level detections. Au and Ag nanoparticles are also utilized in Raman cellular imaging to enhance signal intensity and increase image contrast. However, conventional nanoparticles have inherent limits for in vivo biomolecular SERS imaging in that 1) strong Raman enhancement relies on good coupling between adjacent nanoparticles, so called "hot spots", which is inconsistent for randomly formed nanoparticle clusters; 2) the spatial imaging resolution degrades with increasing size of nanoparticle clusters; and 3) the random distribution of nanoparticles within the biological cell voids the spatial specificity.

Both chemical and conformational information can be elucidated from such SERS data. SERS possesses many desirable characteristics as a tool for the chemical analysis of in vivo molecular species including high specificity, attomole to high zeptomole mass sensitivity, micromolar to picomolar concentration sensitivity, and interfacial generality.

Many current attempts at in vivo sensing detect the molecule of interest indirectly, based on binding events or pH change. The SERS nanostructure sensors of the invention have the advantage of directly detecting the analytes of interest, allowing facile quantification.

The invention provides nanostructures that are biocompatible and incorporate the functional capabilities of nanotip, nanosphere, and nanoring geometries. However, unlike current nanosphere-based SERS spectroscopy and imaging, which uses a wavelength of 500-600 nm, the nanostructures of the invention can be excited at near the infrared range. Excitation at longer wavelengths provides deeper penetration into tissue with minimal photothermal damage, and excitation of the nanostructure does not cause fluorescence of other biomolecules.

The nanostructures of the invention have a higher local field-enhancement factor in the near-infrared wavelength region due to the simultaneous incorporation of SERS hot spots including sharp nanotip and nanoring geometries, leading to the strong hybrid resonance modes from nanocavity resonance modes and tip-tip intercoupling modes. The structures of the invention have a much stronger field emitting or "antenna" effect than previously obtained from nanotips and nanorings. The excited "hotspot" of the structures of the invention have been demonstrated to have an enhancement factor larger than $10^{10}$.

Although the specific examples provided herein demonstrate one particular size of the multilayer composite nanostructure of the invention, one of skill in the art will recognize that the size, shape, and layer thickness can all be individually controlled by modifying the size of a sacrificial nanostructure template, the deposition angle, the deposited layer thickness, and the material of each layer. Since the plasmon-resonance wavelength of the metallic nanostructures is dependent on these parameters, the optical properties of the nanostructure are tunable in the fabrication process of the invention. Referring to FIG. 1, the invention provides a metallic nanostructure 10 comprising an asymmetrical tapered metallic shell 20 comprising one or more metallic materials 30a-d and having at least one opening 40 and a substantially defined edge 50. Although the embodiment depicted in FIG. 1 shows a substantially spherical shape, other geometries can be obtained that fit the general description above (e.g., metallic tapered geometry with at least one opening).

In one aspect, the nanostructure is substantially spherical and has an inner radius r and an outer radius R, wherein said outer radius R is greater than the inner radius r, and wherein the nanostructure has a greater thickness opposite the opening 40 (see, e.g., FIG. 1a), and wherein the edge 50 has a thickness that is less than the thickness of the structure opposite the opening. In one aspect, the nanostructure has the shape of a crescent moon when viewed cross-sectionally, such nanostructures, called "nanocrescent SERS probes" and "nanobowls" herein, may also include two or more layers of different metals (e.g., 30a-d), functional groups attached thereto 60, and have optical or magnetic properties.

Thus, the invention provides nanostructures, such as, for example, a "nanocrescent SERS probe" structure, that enhances detectable signals to facilitate molecular detections. More particularly, the nanostructures of the invention possess geometries, including an edge 50 surrounding an opening, capable of enhancing local electromagnetic fields. Nanosystems utilizing such structures are particularly useful in the medical field for detecting rare molecular targets, biomolecular cellular imaging, and in molecular medicine.

Figure 1C:
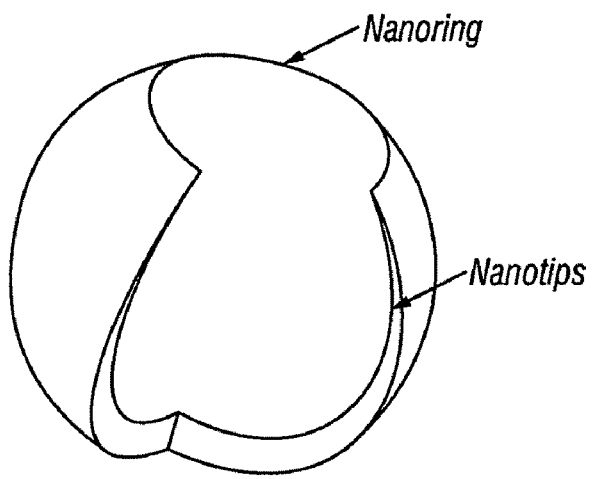

In contrast to other nanostructures, the geometric (e.g., the nanocrescent SERS probe) nanostructures described herein have the features of both nanotips and nanorings that allow for local electromagnetic field enhancement (FIG. 1c). In cross-sectional view, the shape of the nanocrescent SERS probe resembles a crescent moon with sharp tips, so the sharp edge (e.g., 50 see, FIG. 1a) of the nanocrescent SERS probe has the rotational analogy to a sharp tip and it expands the SERS "hot site" from a tip to a circular line (e.g., a group of nanotips) as shown in FIG. 1c. In the top view, the shape of the nanocrescent SERS probe resembles a nanoring with a higher sharpness than existing nanorings, so the circular sharp edge of the nanocrescent SERS probe provides a stronger field emitting or "antenna" effect.

The asymmetric, hollow metallic nanocrescent SERS probes feature a large surface area (for better molecular adsorptions) and a long edge length for the maximized total integration of multiple surface-enhanced Raman scattering (SERS) spectroscopy tips when compared with conventional spherical and/or solid-core nanoshells. Owing to its hollowness, the inner and outer surfaces can be modified with different materials for a wide variety of optical characteristics. Moreover, the sharp edge of the nanocrescent SERS probes results in even higher degree of field enhancement, which is ideal for ultrasensitive, single molecule label-free molecular detection.

The metallic composition of composite nanostructures of the invention are biocompatible, and thus can be biofunctionalized and applied in real-time biomolecular imaging. Unlike conventional fluorescence imaging, Raman spectroscopy acquires unique signatures of chemical and biological molecules without labeling with fluorophore molecules.

Figure 1D:
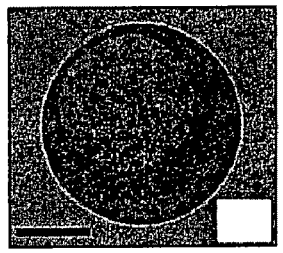
Figure 1E:
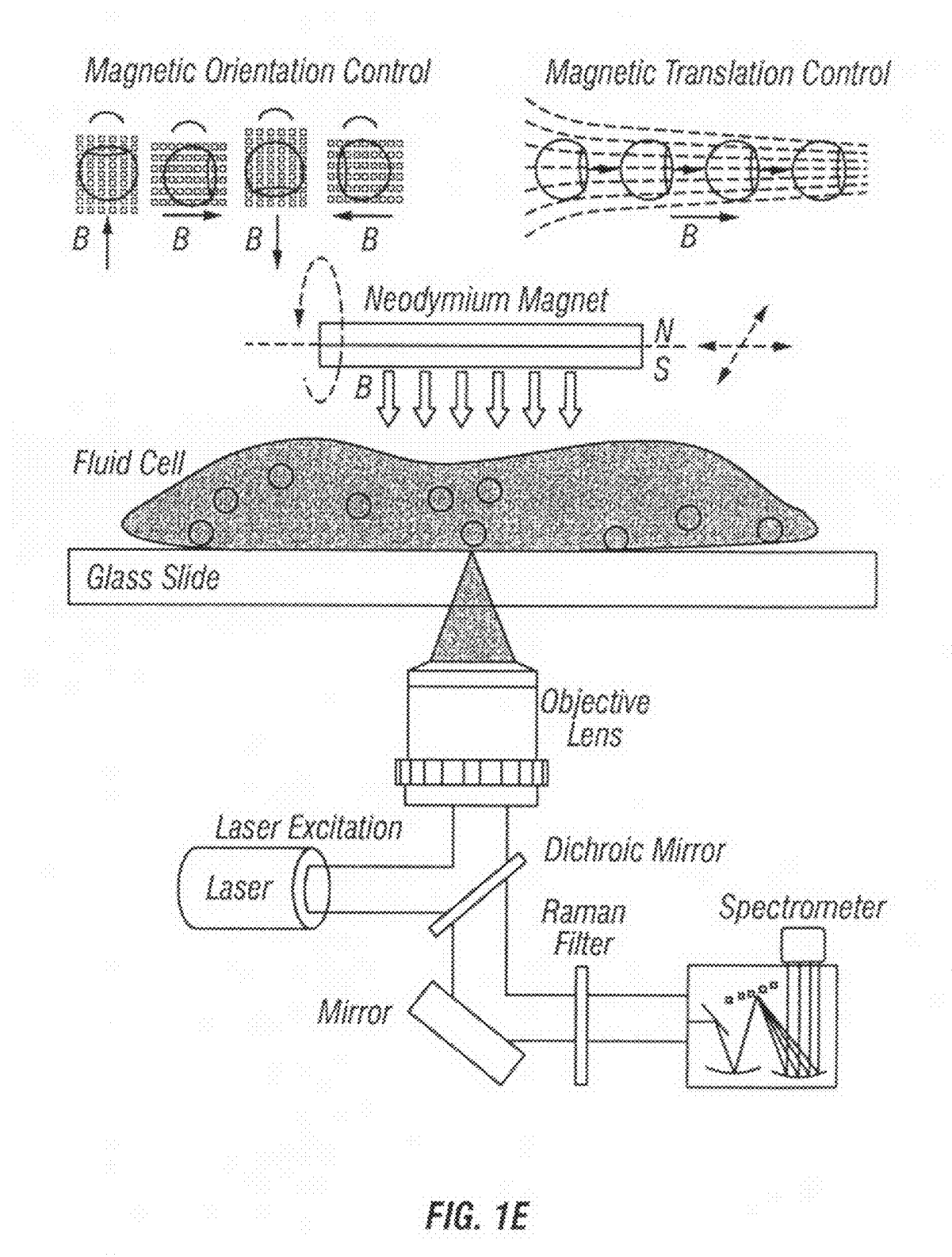

The sub-10 nm sharp edge of gold nanophotonic crescent moons as shown in FIG. 1d incorporates the advantages of both metallic sharp nanotips and ultrathin nanorings, and generates local electromagnetic field enhancement. The fabrication of these sharp-edged metallic nanostructures (e.g., nanocrescent SERS probes) is accomplished by self-assembly of sacrificial nanostructures and conventional thin film deposition method without using e-beam, which allows true batch nanofabrication process.

In addition to the nonfunctionalized nanocrescent SERS probes described above, the nanocrescent SERS probes can be functionalized (i.e. "smart nanocrescent SERS probes".)

The term "functionalized" is meant to include structures with two or more layers of different metals, structures with functional groups attached thereto, structures that have optical properties, magnetic structures, etc.

The nanostructures of the invention (e.g., nanocrescent SERS probes) can optionally be functionalized by imprinting functional groups, such as antibodies, proteins, nucleic acids, and the like, as shown in FIG. 6. Such nanostructures are particularly useful for molecular diagnostics. For example, to prolong or target analyte interaction with the noble metal nanoparticle surface, a binding agent/targeting domain is used to promote interaction of a nanostructure with a desired target. An alkanethiol, such as 1-decanethiol, can be used to form the capture layer on the noble metal (Blanco Gomis et al., J. Anal. Chim. Acta 436:173 [2001]; Yang et al., Anal. Chem. 34:1326 [1995]). Other exemplary capture molecules include longer-chained alkanethiols, cyclohexyl mercaptan, glucosamine, boronic acid and mercapto carboxylic acids (e.g., 11-mercaptoundecanoic acid).

Alternatively, a self-assembled monolayer (SAM) is formed on the nanostructure surface to concentrate the analyte of interest near the surface of the nanostructure. Exemplary SAMs include, but are not limited to, 4-aminothiophenol, L-cystein, 3-mercaptopropionicacid, 11-mercaptoundecanoic acid, 1-hexanethiol, 1-octanethiol, 1-DT, 1-hexadecanethiol, poly-DL-lysine, 3-mercapto-1-propanesufonic acid, benzenethiol, and cyclohexylmercaptan. Typically the SAM is comprised of straight chain alkanethiols.

In other embodiments, nanostructures of the invention are coated to inhibit the accumulation of biological material (e.g., proteinaceous agents) on the nanostructure's surface. In some embodiments, polyethyleneglycol (PEG) is immobilized on nanostructure surfaces to prevent nonspecific interactions. In some embodiments, silica sensor surfaces not coated with silver are PEGylated with silane terminated monomethoxyPEG and silver coated nanoparticle surfaces are coated with oligoethyleneglycol terminated alkanethiols.

Attached functional groups 60, can comprise components for specifically, but reversibly or irreversibly, interacting with the specific analyte 70 (e.g., can be labeled for site/molecule directed interactions). For example, a surface bound functional group 60 (e.g., a targeting ligand) can be attached to a nanostructure of the invention. For example, a chemical molecule can be immobilized on the surfaces of a nanostructure of the invention. The invention demonstrates that a self-assembled monolayer of 3-mercaptopropyltrimethoxysilane (MTMO), a thiol-group containing molecule, can be attached to the surface of the nanostructure through Au sulfide bonds by spreading and drying a droplet of 1 lM MTMO in anhydrous ethanol solution. FIG. 3c shows the SERS spectra of MTMO molecules on the background substrate and the nanocrescents in two different orientations. The spectra were taken using a laser excitation with 1 mW power and an integration time of 20 s. In accordance with the trend shown in the far-field scattering intensity measurement, it can be seen that the SERS enhancement factor of the perpendicularly oriented nanocrescent is higher than that of the obliquely oriented nanocrescent by comparing the intensity of 637 cm-1 Raman peak.

A targeting ligand can include a receptor bound to the surface of a nanostructure of the invention that interacts reversibly or irreversibly with a specific analyte. Typically, the interaction of the targeting ligand and the analyte lasts sufficiently long for detection of the analyte by SERS.

Examples of functional groups (e.g., targeting ligands) include antigen-antibody pairs, receptor-ligand pairs, and carbohydrates and their binding partners. The binding ligand may be nucleic acid, when nucleic acid binding proteins are the targets. As will be appreciated by those in the art, the composition of the binding ligand will depend on the composition of the target analyte. Binding ligands to a wide variety of analytes are known or can be readily identified using known techniques.

For example, when the analyte is a single-stranded nucleic acid, the binding/targeting ligand is generally a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, may be used, either as the analyte or the functional group (e.g., targeting/binding ligand). Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. In one embodiment, the binding ligands are portions (e.g., the extracellular portions) of cell surface receptors.

Analytes that can be detected or measured by the compositions and methods of the invention include any molecule or atom or molecular complex suitable for detection by the nanostructures of the invention. Examples of such analytes include, but are not limited to, biomolecules such as proteins, peptides, polynucleotides, lipids and the like, glucose, ascorbate, lactic acid, urea, pesticides, chemical warfare agents, pollutants, and explosives.

In some embodiments, the invention provides kits and systems for use in monitoring the level of an analyte in a sample or subject. In some embodiments, the kits are for home use by a subject to assist in identifying an analyte, disease or disorder or to monitor a biological condition. For example, in some embodiments, a sensor is delivered to the subject (e.g., by a medical professional) and the subject is provided with a device for monitoring levels of an analyte (e.g., the subject places the device near the nanostructure location or suspected location and the device provides a reading of the level of the analyte).

The invention has use in the detection of analytes in the environment, including explosive and biological agents. Accordingly, the invention is useful in Homeland Security and the military for detection of analytes. In one embodiment, the invention provides kits for monitoring military personnel in a war situation where they may be exposed to toxins. The nanostructures are administered or contacted with the subject prior to potential exposure. The subjects can then be monitored at set intervals using a detection device.

The invention further provides magnetically controllable nanostructures of the invention by incorporating composite layers with a ferromagnetic material (see, e.g., FIG. 1a). A nanostructured composite multilayer design such as, for example, Au/Ag/Fe/Au allows an ideal biophotonic molecular probe controllable with an external magnetic field. The fabrication process of a composite nanocrescent is further provided by the invention.

Figure 3:
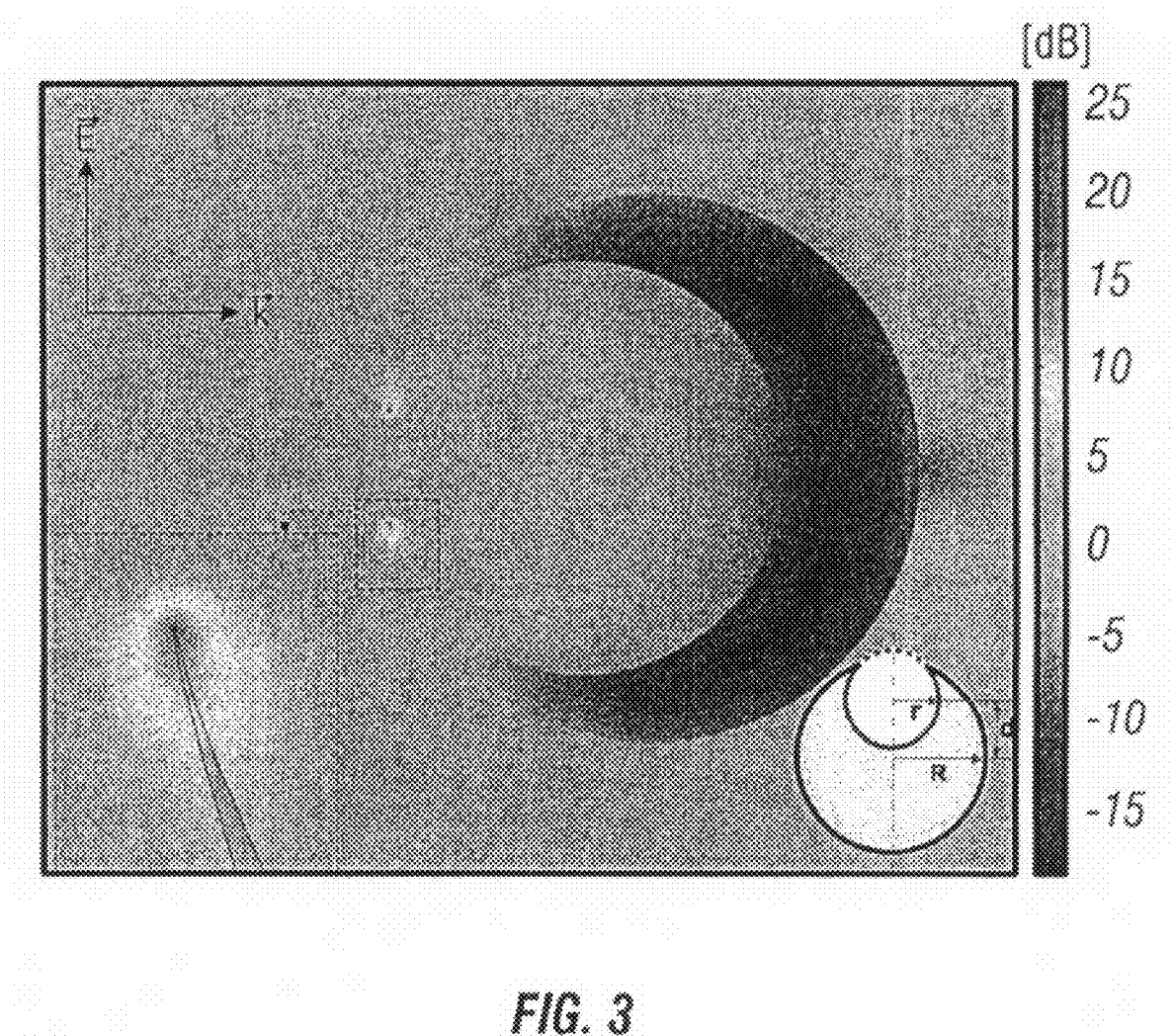
FIG. 3 shows local electric field amplitude distribution of a nanocrescent SERS probe at one of its scattering peak wavelength (785 nm). The geometry of the nanocrescent SERS probe is shown in the inset schematics where r is the inner radius, R is the outer radius and d is the center-center distance as shown as two partially overlapping circles. For this nanocrescent SERS probe, r=150 nm, R=200 nm, d=51 nm. The shown field amplitude is normalized with respect to the incident field amplitude. The direction of light incidence is from left to right.

Since the orientation of suspended nanostructures (e.g., nanocrescents) of the invention can be controlled dynamically by an external magnetic field, the SERS signal can be modulated magnetically. For example, after a nanostructure (e.g., a nanocrescent) is stabilized under a constant magnetic field, the SERS spectra from a single structure can be continuously taken while the orientation of the external magnetic field is changing. The integration time of spectra acquisition is about 10 seconds. In one aspect, a spectrum is taken after the magnet rotates for approximately 20°. FIG. 3$d$ shows a series of SERS spectra recorded as a function of time. The intensity of the 637 $cm^{-1}$ Raman peak varies periodically and responds to the rotation of the magnet.

Accordingly, Raman peak intensities can be improved through magnetic modulation, which is useful when the Raman peaks from a complex background are as high as those of a target molecule.

Furthermore, the magnetic nanostructures of the invention can be precisely manipulated with proper magnetic field control. As discussed herein, the biocompatible surface (e.g., an Au surface) can also be functionalized by tethering/attaching oligonucleotides, peptides, or antibodies using well-established methods.

Because of the above reasons, the biochemical composition of the local intracellular environment at the nanometer scale can be measured by the translocation of standalone magnetic nanostructures of the invention to a desired position within living cells and detecting the fingerprints of biomolecules dynamically. The orientation modulation of nanostructures by magnetic fields can further increase the signal-to-noise ratio in the dynamic SERS detections.

In one aspect, the nanostructure comprises a multilayer of 10 nm Au, 10 nm Fe, 20 nm Ag, and 10 nm Au. The choice of materials and multilayer thickness are selected based, in part, upon the finite-element simulation in order to tune the plasmon-resonance wavelength of the composite nanostructure matched with the excitation wavelength. Typically the nanostructure (e.g., the nanocrescent) has a sub-10 nm sharp edge. The nanostructures (e.g., nanocrescents) can then be controlled by magnetic fields during SERS imaging (FIG. 1$e$).

Excitation of the nanostructures of the invention is performed by contacting the nanostructure with appropriate electromagnetic radiation (e.g., an excitation wavelength). Wavelengths in the visible spectrum comprise light radiation that contains wavelengths from approximately 360 nm to approximately 800 nm. Ultraviolet radiation comprises wavelengths less than that of visible light, but greater than that of X-rays, and the term "infrared spectrum" refers to radiation with wavelengths of greater 800 nm. Typically, the desired wavelength can be provided through standard laser and electromagnetic radiation techniques.

In contrast to spherical metallic nanoparticles, the nanostructures (e.g., nanocrescents) of the invention have plasmon resonance modes in the near-infrared wavelength region and a much higher local field enhancement (about 20 dB of electric-field amplitude). The enhancement factor and local field distribution are dependent on the orientation of the nanostructures with respect to the incident direction of excitation energy (e.g., light), as shown in the finite element simulation (FIG. 3$a$). A FEMLAB electromagnetic simulation software (COMSOL, California) was used to generate the results. The maximum local field enhancement was achieved when the propagation direction of the excitation field is parallel to the symmetry line of the nanostructure. In an experiment, a circularly polarized near-infrared laser (785 nm) is focused on the nanostructures by a high numerical aperture (NA) microscopy objective lens. No optical filter is used in this measurement. The local field intensity measured from the far field shows that the enhancement by a single nanostructure of the invention, shown in the right image of FIG. 3$b$, is greater than fivefold, which cannot be attributed to reflections from the metallic surface, because reflection becomes negligible and scattering dominates for structures much smaller than the excitation wavelength. In contrast, another nanostructure of the invention, shown in the middle image of FIG. 3$b$, only generates a two- to three-fold enhancement, possibly due to a different orientation, which verifies that the local field enhancement of a composite nanostructure depends on their orientations. The inset drawings in FIG. 3$b$ illustrate the possible orientations of these two nanostructures, and the cross-line intensity plots further clarify the orientation-dependent field enhancement effect. In comparison, 80 nm Au nanospheres were also tested, but no significant field enhancement effect was observed at the 785 nm excitation wavelength.

The nanostructures of the invention can be used in vivo and in vitro to detect, identify, and/or characterize analytes of interest. The nanostructures can be used to detect analytes in environmental samples as well as samples derived from living organisms. As used herein, the term "sample" is used in its broadest sense. For example, a sample can comprise a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. The nanostructures can be used, for example, in bodily fluids in vivo or in vitro. Such bodily fluids include, but are not limited to, blood, serum, lymph, cerebral spinal fluid, aqueous humor, interstitial fluid, and urine.

Commercial applications include environmental toxicology, materials quality control, food and agricultural products monitoring, anesthetic detection, automobile oil or radiator fluid monitoring, hazardous spill identification, medical diagnostics, detection and classification of bacteria and microorganisms both in vitro and in vivo for biomedical uses and medical diagnostic uses, infectious disease detection, body fluids analysis, drug discovery, telesurgery, illegal substance detection and identification, and the like.

A number of devices can be used for Raman spectroscopy. Any device suitable for detection of a signal from the nanostructure of the invention. In some embodiments, the device includes delivery and collection optics, a laser source, a notch filter, and detector.

One method of making a nanostructure of the invention is depicted in FIG. 2. Template nanostructures 100 are used in the methods of the invention. A photoresist material 110 on a substrate 120 is used to support the template nanostructures 100 during deposition of the desired material (e.g., noble metal). In FIG. 2B the desired material 130 (e.g., gold) is deposited on the nanostructure template 100 at a desired angle. Typically the angle will be calculated to obtain a particular sharp edge on the portion of the nanostructure template in contact with the photoresist material. The photoresist 110 and substrate 120 are rotated at a desired speed to allow deposition of the material to all sides of the nanostructure template not in contact with the photoresist 110. Once the deposition process is complete the coated nanostructures 140 are removed from the photoresist 110. In one aspect, the template nanostructure is degraded to provide a hollow nanostructure of the invention. In other embodiments, the template nanostructure remains intact.

The invention thus provides a method for making nanostructures of the invention comprising providing a template nanostructure 100 (e.g., a spherical template nanoparticle) to a surface; depositing one or more metallic materials onto the template to form coated nanoparticle 140; and disassociating the coated nanoparticle from the surface. The nanostructures may be used with or without decomposing the template material. Batch fabrication is straightforward and does not require e-beam lithography. These characteristics make the nanostructures of the invention useful for application in molecular medicine and in ultrasensitive Raman, biomolecular, and cellular imaging.

In one aspect, the nanostructure (e.g., nanobowl) are fabricated by rotational deposition of a thin noble metal layer on polymer nanostructures template 100 at certain angles and subsequent dissolution of the sacrificial nanosphere templates 100 as shown in FIG. 2. Though the nanocrescent SERS probes with certain dimension are exemplified, the inner diameter and thickness of nanostructure (e.g., nanobowl) can be controlled in the fabrication by choosing the size of the nanostructure templates as well as the deposition thickness and angle. The structures of the nanocrescent SERS probes maintain their original shape and do not collapse during the process of dissolving the sacrificial nanostructure templates or redistributing on a surface for imaging. While gold nanocrescent SERS probes are exemplified herein, it is understood that other metals, either alone or in combination, can be substituted for gold.

In one embodiment, the invention provides a biocompatible metallic composite (e.g., Au/Ag/Fe/Au) nanostructure, which can not only function as a stand alone SERS substrate with integrated SERS hot-spot geometries, but can also be controlled magnetically to produce orientational and translational motions. A single nanocrescent demonstrates a SERS enhancement factor higher than $10^8$ in the detection of sub-zeptomole molecular concentrations. Magnetically modulated SERS detection of molecules on a single composite nanocrescent probe is also demonstrated by the invention.

Various polymers may be used as the template nanostructure in the generation of a nanostructure of the invention. For example, o-polyacrylamide and poly(vinyl chloride), poly (vinyl chloride) carboxylated, polystyrene, polypropylene and poly(vinyl chloride-co-vinyl acetate co-vinyl) alcohols, may be used.

The SERS nanostructures of the invention are coated with a noble metal. In some embodiments, the metal is silver or gold. However, the invention is not limited to the use of silver or gold. Any noble metal may be utilized, including, but not limited to, platinum. In certain embodiments, a 1 mm layer of titanium or chromium is added to the surface of the particles prior to application of the noble metal (e.g., gold or silver) in order to improve the adhesion of the silver to the surface of the polymer.

Several groups demonstrated a significant field enhancing effect by nanotips and nanorings in their numerical simulations and experiments. Since the nanocresent moons of the invention have the geometrical features of both nanotips and nanorings on the sharp edge area, an excellent local field enhancement from that area is generated. FIG. 3 shows the simulated electric field amplitude on a sharp-edged gold nanocrescent SERS probe (300 nm inner diameter and 100 nm bottom thickness) with a 785 nm NIR laser excitation.

Figure 6A:
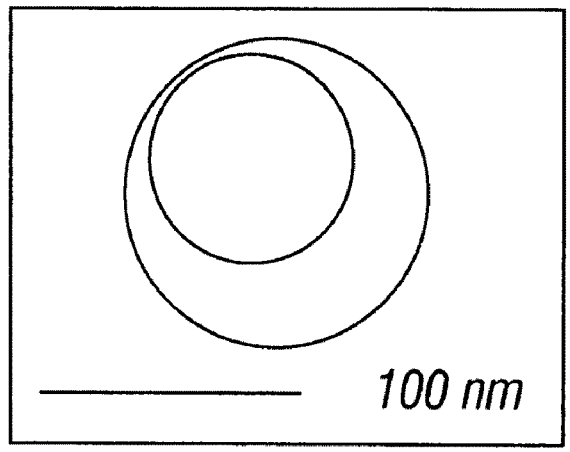
FIG. 6A-D shows images of nanostructure (e.g., nanobowl). (a) TEM image of Au nanostructure (e.g., nanobowl) after removing sacrificial template, (b) Au with selective patterning of functional group (FG) by molecular imprinting, (c) Au/Ag/Au/FG for better SERS enhancement, and (d) Au/Fe/Ag/Au/FG for spatial control by nanoelectromagnetic circuit.
Figure 6B:
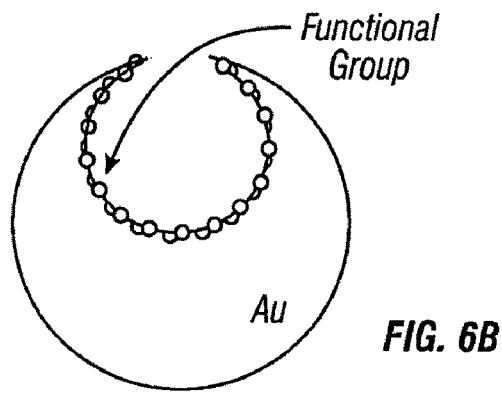
Figure 6C:
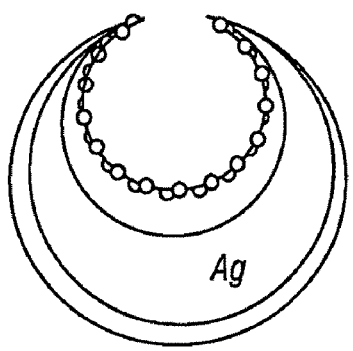
Figure 6D:
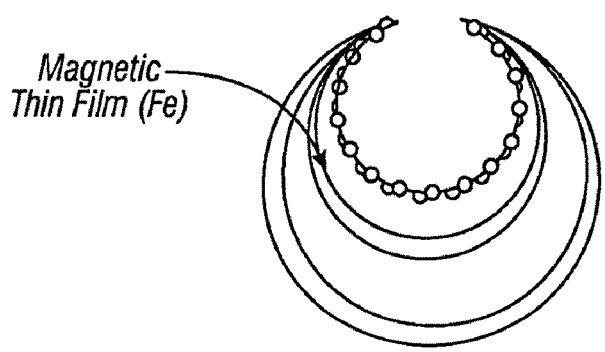
Figure 7:
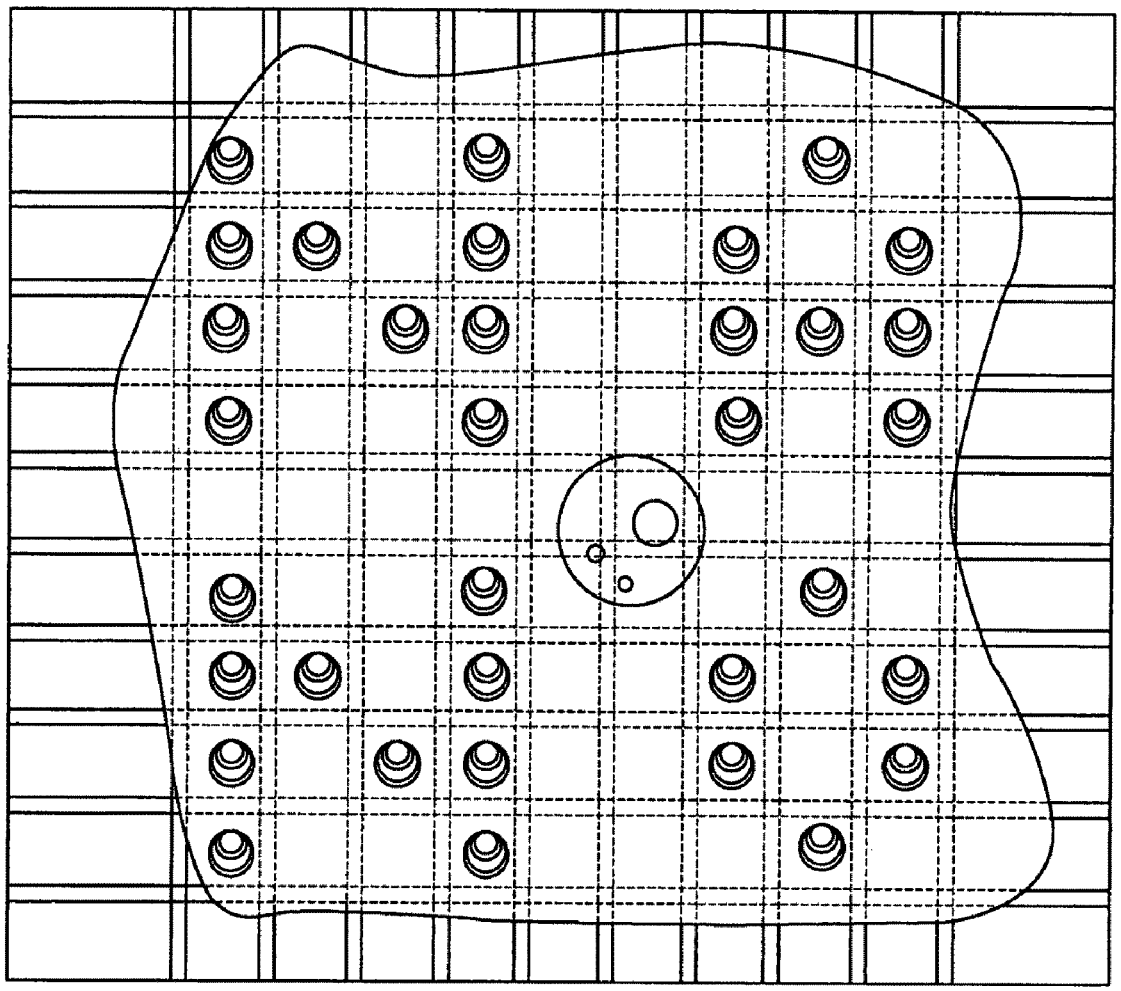
FIG. 7 shows a schematic diagram of nanostructure (e.g., nanobowl) (Au/Fe/Au/FG or Au/Ag/Fe/Au/FG) and nanoelectromagnetic circuit to control the position of nanostructure (e.g., nanobowl) inside of cell as well as local temperature perturbation capability via NIR modulation of "hot spot" of nanostructure (e.g., nanobowl) for advanced molecular imaging and drug delivery.
Figure 8A:
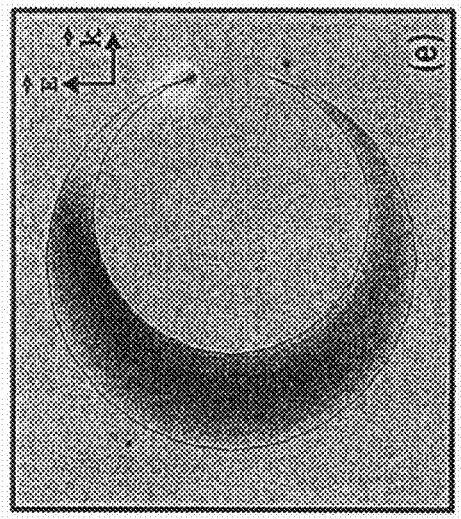
FIG. 8A-E shows a gold nanostructure (e.g., nanobowl) under the excitation by a near infrared (785 nm) TM wave is simulated using the 2-dimensional finite element method. The shape of the nanostructure (e.g., nanobowl) is specified by r=150 nm, R=200 nm, d=51.23 nm (see the inset for the definitions of the geometric parameters). The surface plots represent the spatial variation of the local field enhancement factor ($10 \cdot \log [E_{local}/E_{incident}]$) due to the nanostructure (e.g., nanobowl) as a function of the excitation angle. The directions of propagation and polarization are specified in each plot. Up to 25 dB field enhancement is observed near the tip. The enhancement inside the cavity depends strongly on the incidence angle. From (a) to (e), the incidence angle changes from 0 to 180 degrees with a 45 degree increment. In the case of (c), the in-cavity field enhancement factor is maximized at approximately 10 dB.
Figure 8D:
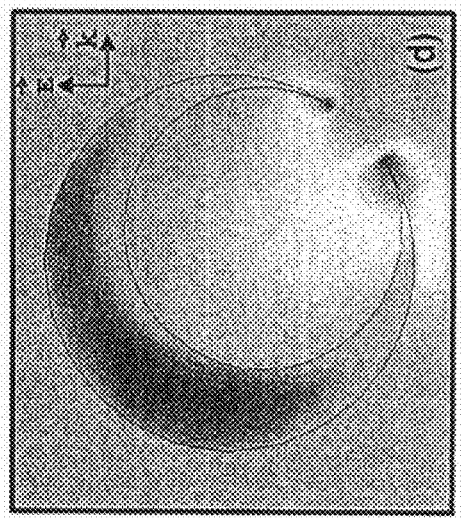
Figure 8C:
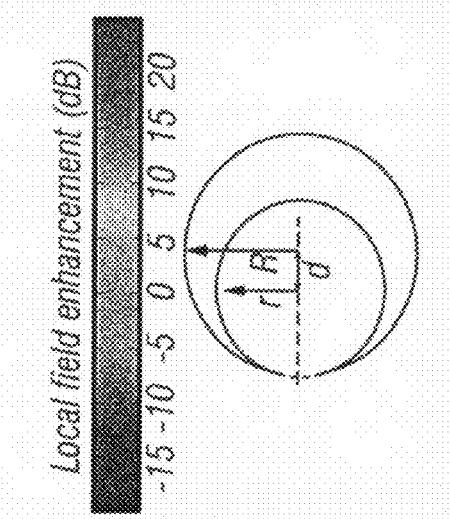
Figure 8B:
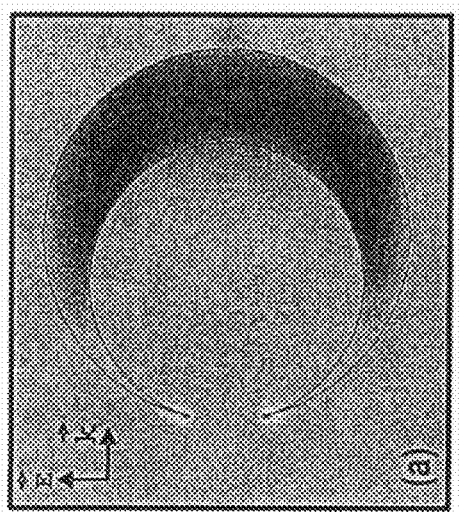
Figure 8E:
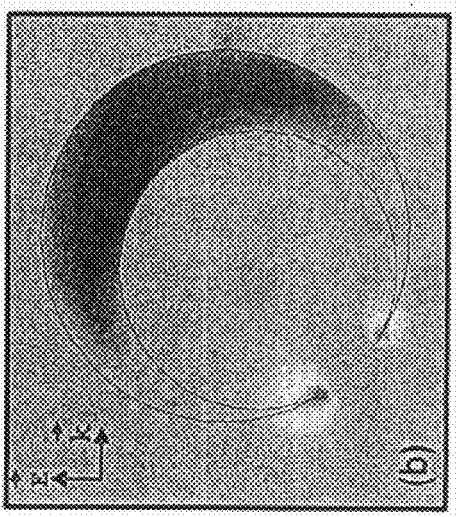

The nanocrescent SERS probes can also be spatially controlled by a nanoelectromagnetic circuit by including a magnetic layer, such as Fe, as shown in FIG. 6d. Such nanocrescent SERS probes can be spatially and temporally controlled as depicted in FIG. 7 using a nanoelectromagnetic circuit. Such nanostructure (e.g., nanobowl) can be positioned in an array, and can also be manipulated inside cells for advanced molecular imaging and drug delivery applications. Optomagnetic nanocrescent SERS probes can be constructed as shown in FIG. 6d with, for example, Ni, Co and Fe components.

As shown in FIG. 8, image enhancement can be easily manipulated by altering the direction of such nanocrescent SERS probes to localize field enhancement in a predictable manner.

Arrays and nanofluidic devices of nanocrescent SERS probes are also contemplated by the invention. The invention provides an optofluidic application based on a direct optical-to-hydrodynamic energy conversion using suspended photothermal nanoparticles of the invention near the liquid-air interface. Using light beams with submilliwatt power, the invention provides fluidic devices that can drive and guide liquid flow in microfluidic channels to transport biomolecules and living cells at controlled speeds and directions. The invention provides methods that dispense with the need for complex pump and valve devices, surface chemistry and electrode patterning, or any other further effort towards substrate fabrication. Instead, the optofluidic control method of the invention will allow the fabrication of all-optical large-scale integrated microfluidic circuits for biomolecular and cellular processing without any physical valve or mechanical pumping device.

Figure 14A:
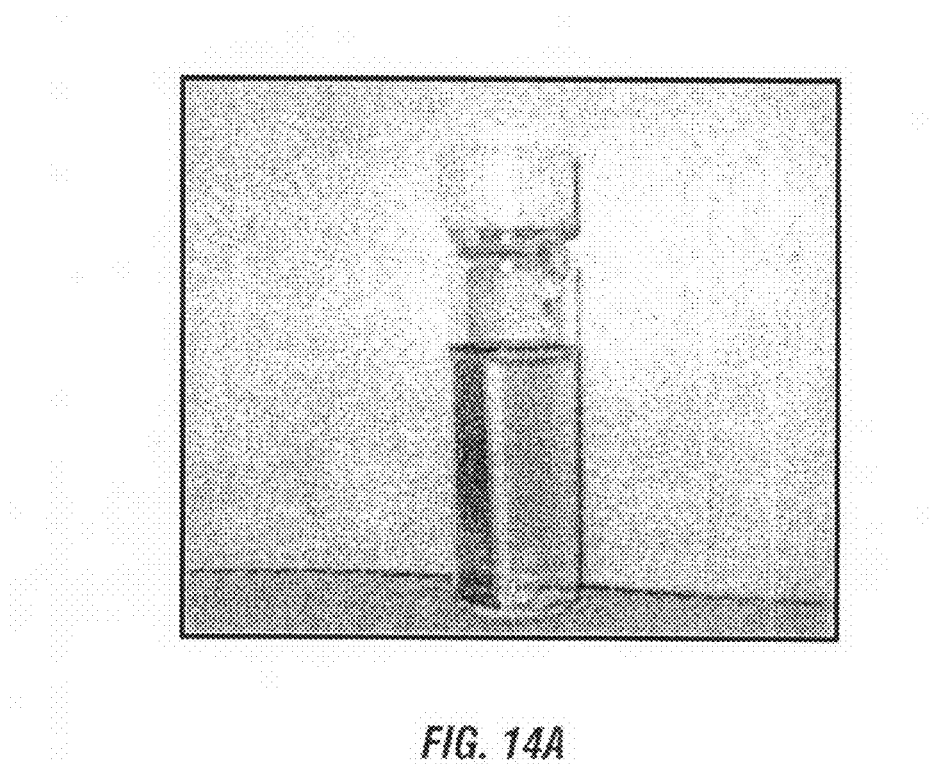
FIGS. 14A-B demonstrates the optical properties of the PNP suspension (gold nanocrescent particles). A) True color picture of 1 nM PNP suspension. B) Absorption spectrum of 1 nM PNP suspension.
Figure 14B:
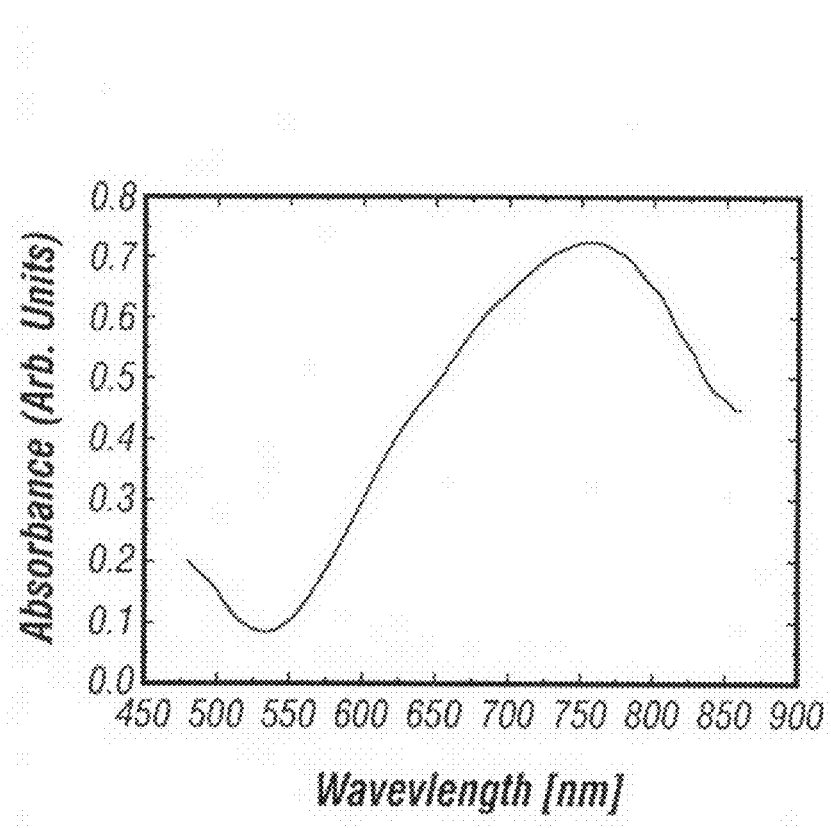

The fluidic aspect of the invention utilizes nanostructures of the invention having a strong absorption band around 780 nm (see FIG. 14) as the photothermal nanoparticles (PNPs). The nanostructures used in the fluidic aspect of the invention are not necessarily limited to the particular nanobowls/nanocrescent structures of the invention. One of skill in the art will recognize that many other nanoparticles with potential photothermal properties such as Au nanoshells, nanorods, nanocages, nano-half-shells as well as carbon nanotubes can also be used as PNPs in optofluidic control. The PNP-activated optofluidic effect simultaneously involves, for example, evaporation, condensation, coalescence, contact-line pinning, surface wetting within the millisecond timescale and micrometer dimension. This mechanism is fundamentally different from that of Marangoni flow in which the liquid is driven by a surface-tension gradient.

Figure 9A:
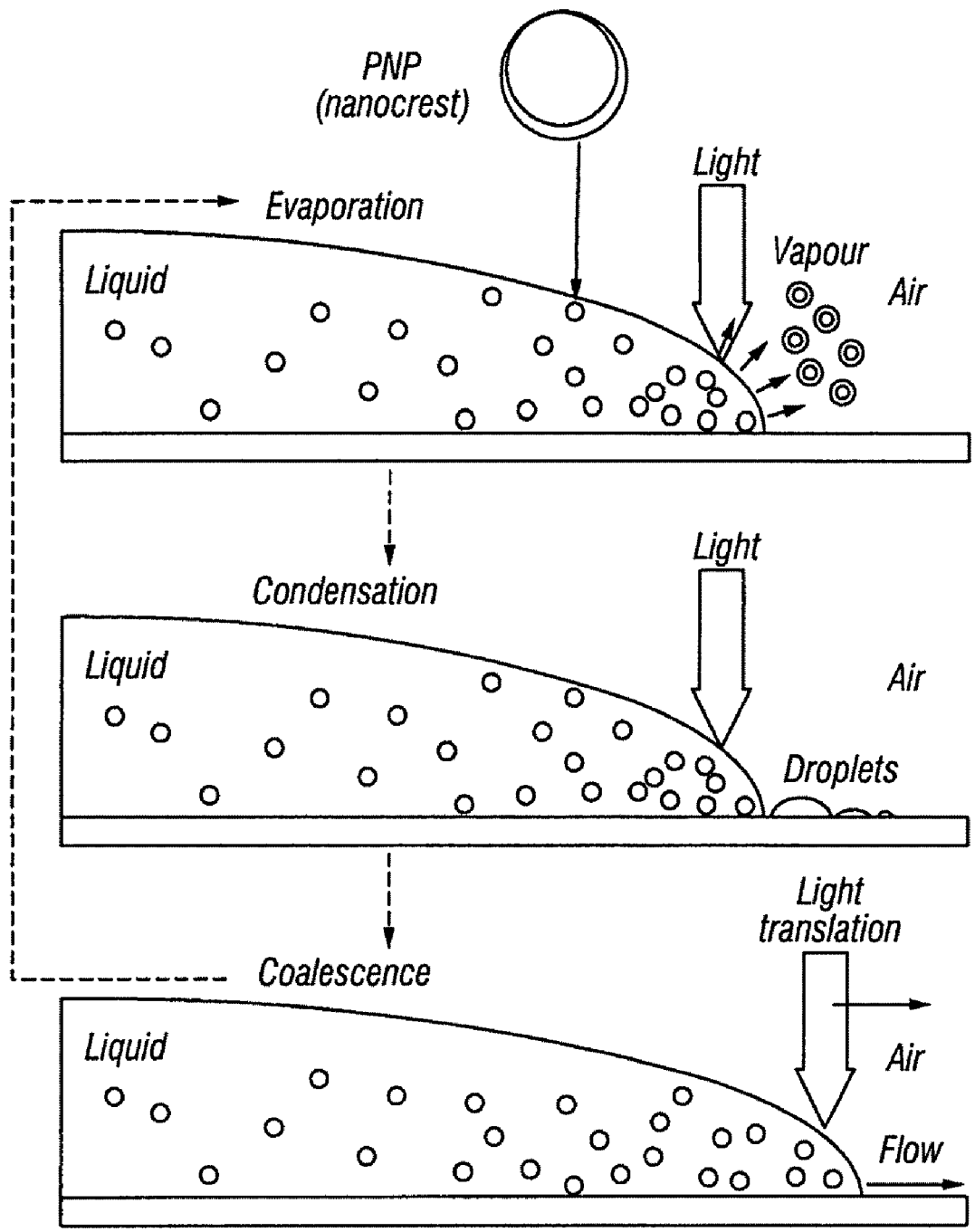
FIG. 9A-C shows photothermal nanoparticle (PNP) activated optofluidic flow using nanostructures of the invention. A) The principle of the optically controlled advance of the liquid-air interface. First, the focused light illumination on the PNPs increases the local temperature of the liquid and leads to water evaporation at the liquid-air interface. Second, the vapour in the relatively cold air condenses into droplets in front of the liquid-air interface. Third, the droplets coalesce with the original bulk liquid body and the liquid-air interface advances. The processes are repeated as the light is translated, so the optofluidic flow can be continuous. B) Video prints showing the light-driven advance of the liquid-air interface of a 1 nM PNP water solution on a glass surface. C) The temperature distribution in PNP-suspended liquid with the focused light illumination. The fluorescence images show a liquid containing 1 M HEPES, 100 μM fluorescein and 1 nM PNPs respectively (i) before and (ii) after 1-s focused illumination of 20 mW, 785 nm laser light on the area marked by the red circle. The color-coded image in (iii) is the temperature distribution after the light illumination. All scale bars are 10 μm.

The mechanism of the PNP-activated optofluidic effect is as depicted in FIG. 9a. At the beginning, the liquid on a hydrophobic surface remains stationary. The local concentration of PNPs near the liquid-air interface is higher than that of the interior owing to the 'coffee-ring' effect. When a focused light illuminates the PNPs near the liquid-air interface, heat is generated and transferred from the PNPs to the surrounding liquid within tens of nanoseconds, which significantly accelerates the liquid evaporation from the interface and produces vapour. In contrast, the original liquid contact line is pinned and liquid lost in evaporation is replenished from the interior region.

The vapour in the colder air condenses almost immediately after the evaporation and droplets form very close to or even in contact with the liquid-air interface. The droplets then coalesce with each other and grow into larger ones that eventually merge with the original liquid body and extend its contact line. Previous studies have shown that the droplet coalescence can facilitate flow significantly, and the surface wetting by the coalesced droplets also assists the advance of the liquid-air interface. The PNPs are drawn towards the new contact line because of the liquid motion and convection. The above processes can occur repeatedly and concurrently, and the liquid flow can be continuous if the light illumination is translated along with the advancing liquid-air interface.

Hence the optofluidic control method can be applied to transport liquid containing biomolecules and cells with their original integrities.

As polydimethylsiloxane (PDMS) microfluidic chips fabricated by soft lithography have been extensively used in chemical, biomolecular and cellular analysis, the invention demonstrates the optofluidic control of PNP-suspended liquids in PDMS microfluidic chips. Unlike the unconfined flow of a millimeter-scale liquid drop, the optically controlled fluidic flow in predefined microchannels is laminar and unidirectional. It shows a much higher flow speed as the vapour and droplets are bound within the channel and contribute to the liquid advance only along the channel direction and the minimized vertical convection in microchannels favors the heat concentration at the liquid-air interface.

Microfluidic channels can be formed in any number of materials. Thus, the devices of the invention include at least one flow channel that allows the flow of sample to other channels, components or modules of the system. As will be appreciated by those in the art, the flow channels may be configured in a wide variety of ways, depending on the use of the channel. For example, a single flow channel starting at a sample inlet port may be separated into a variety of smaller channels, such that the original sample is divided into discrete subsamples for parallel processing or analysis. Alternatively, several flow channels from different modules, for example, the sample inlet port and a reagent storage module may feed together. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer flow channels can be used.

In one embodiment, the devices of the invention include at least one inlet port for the introduction of a sample to the device. This may be part of or separate from a sample introduction or a sample mixing chamber.

Figure 10A:
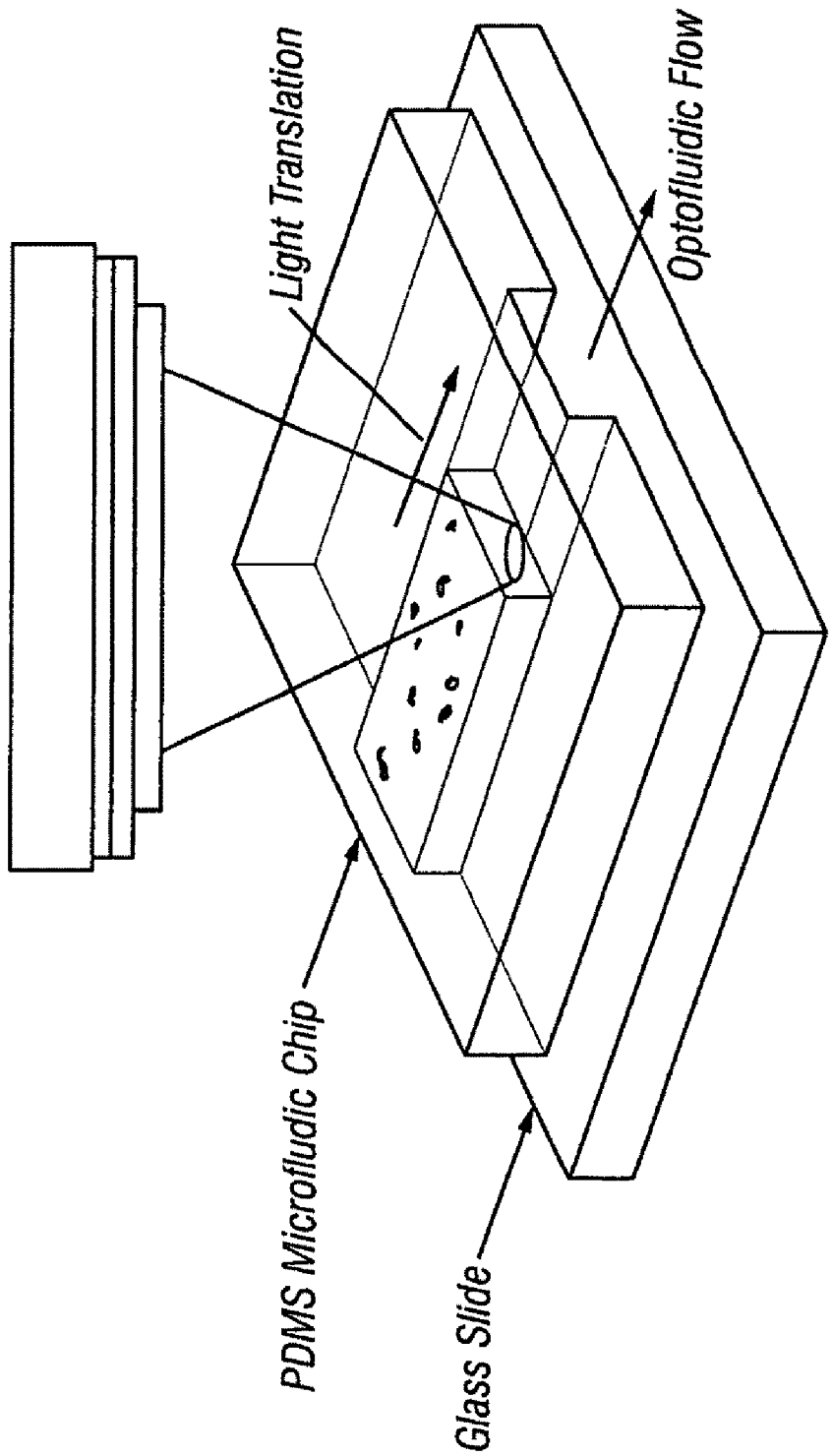
FIG. 10A-E shows Optofluidic control in straight microfluidic channels. A) Illustration of an experimental system configuration. B) Optofluidic control in a 40-μm-wide channel. The video prints show that the flow of the 0.5 nM PNP-suspended 1×PBS buffer solution follows the optical guiding of a 10 mW, 785 nm laser spot at a speed of ~50 μm s$^{-1}$ (frames 1-5) and stops otherwise (frame 6). C) Optofluidic control in an 80-μm-wide channel. The 1 nM PNP water solution is guided by a 10 mW, 785 nm laser spot at a speed of ~50 μm s$^{-1}$. D) Simultaneous optofluidic controls of 1 nM PNP water solutions in two parallel 10-μm-wide channels by a focused laser line with sub-milliwatt illumination power on each channel. Other channels are intentionally left empty for better image contrast. Frames 1 and 2 show the channels respectively before and after the light translation at a speed of ~10 μm s$^{-1}$. E) Optofluidic control of four different liquids. From top to bottom, 0.2 nM and 1 nM PNP water solution, pure deionized water and 60-nm Au colloidal nanospheres are introduced into the 10-μm-wide channels, respectively. Frames 1 and 2 show the channels respectively before and after the light translation at a speed of ~10 μm s$^{-1}$.

In another aspect of the invention, the devices of the invention may include a manipulation chamber that allows for the mixing of PNPs and a fluid sample. For example, in one aspect, the microfluidic channels are formed by directly placing a PDMS slab (on which the water contact angle is 110°, see FIG. 17) with recessed grooves on the hydrophobic glass slide (FIG. 10a).

The liquid remains stationary in the hydrophobic channel without the light guide owing to the balanced surface energy, and no thermocapillary flow is seen when the light spot illuminates the interior of the liquid. The liquid flow stops immediately after the light translation stops, and liquid motion in the microchannel is under complete control without any valve or pump. As the light illumination power, microchannel dimension and PNP concentration are three major tunable factors to determine the rate of droplet formation and coalescence, thus characterizing the optofluidic flow speed. FIG. 11a shows the maximal speed of the optofluidic flow versus the power of light illumination for 1 nM PNP solutions and FIG. 11b shows the maximal flow speed versus the PNP concentration for 20-mW illumination power. The flow speed can be further increased by adopting narrower microchannels, more accurate light control and PNPs with higher photothermal efficiency.

Figure 12A:
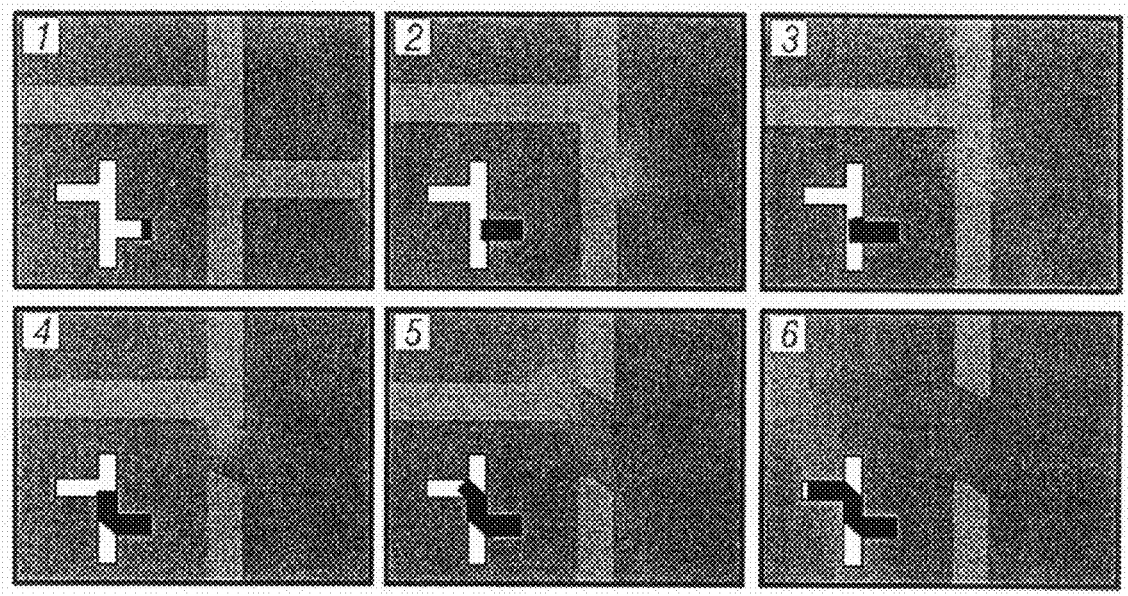
FIG. 12A-C shows the optofluidic control at two adjacent T-shaped channel junctions. A) Video prints showing that a 1 nM PNP water solution introduced from the right channel is optically guided into the left channel after two sharp turns without filling the other two channels. B) Optofluidic control of liquid flow into three distinct paths at the two junctions without filling undesired channels. C) Optofluidic mixing of three separate liquid streams into one.
Figure 12B:
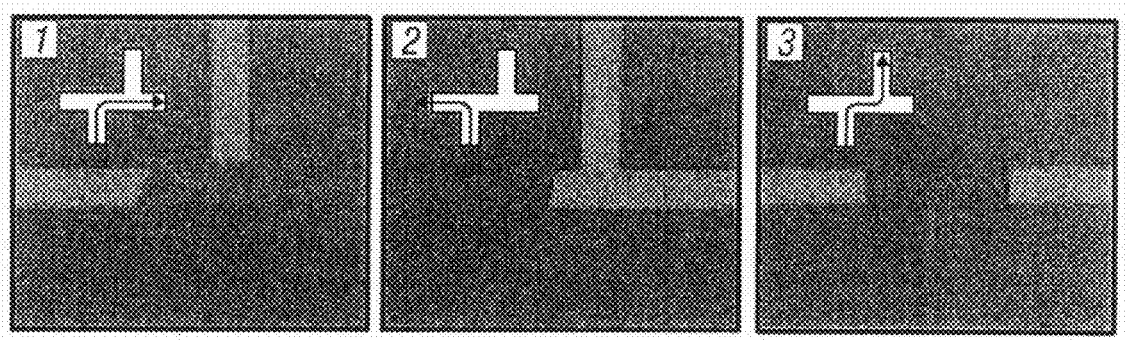
Figure 12C:
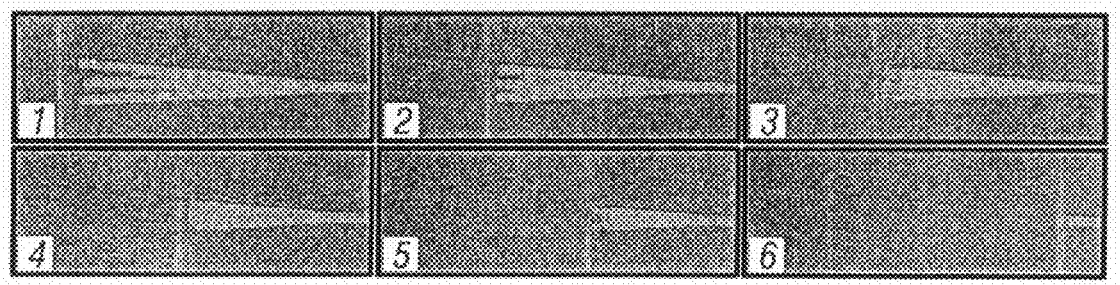

In addition to individual straight channels, a functional microfluidic circuit often consists of channel junctions. The positioning of liquid flow at channel junctions requires complicated valve systems. The invention overcomes the complicated valve channels using optofluidic control with superior directionality at the channel junctions without any valve or pump. Among the channel junction structures, the mixer is one of the most common components in microfluidic biochips. Here, we demonstrate that the liquids in three respective channels can be mixed with optofluidic control as shown in FIG. 12c. The optofluidic flow speed becomes much faster after the liquid mixing, which indicates that the PNPs in the three fluids mix together and become concentrated. Thus, the PNP-activated optofluidic control can be realized in a microfluidic 'maze' with many junctions in various shapes.

Not only can soluble molecules be transported in microfluidic devices with optofluidic control, but living cells can also be transported. In order to test the cell viability when co-cultured with PNPs, three types of cell, Jurkat T-cells, Chinese hamster ovary cells and HeLa cells, were stained with Calcein AM green fluorescent dye. Gold-based PNPs have negligible toxicity to these three cell lines after an incubation of 24 h, and the cells can still proliferate. The gold-based nanoparticles. The optofluidic transportation of single and multiple Jurkat T-cells with PNP-suspended culture media in 100-μm-wide, 50-μm-high PDMS channels is demonstrated by the invention. Most of the cells can be transported intact (no fluorescence intensity decrease), even including those that are only several micrometers away from the laser spot. Some of cells can adhere to the surface and are alive after the attachment. The other two types of cell, Chinese hamster ovary cells and HeLa cells, were also tested and can be transported in the similar fashion.

The optofluidic control using PNPs in nano- or microfluidic circuits allows the creation of a large-scale all-optical biofluidic microprocessor for biomolecular and cellular medicine. With the assistance of laser beam scanning or spatial light modulation apparatus, automated and multiplexed optofluidic controls with high precision can be realized. The complexity and cost of the microfluidic biochips can be greatly reduced using complete optofluidic control. In addition to applications in biochips, the optohydrodynamic energy-conversion scheme using metallic nanoparticles also has implicational importance to nano and microscale water power systems, solar heating systems and other optically powered nanomachines in aqueous environments.

A nanostructure of the invention can be formulated with a pharmaceutically acceptable carrier, although the nanostructure may be administered alone, as a pharmaceutical composition.

A pharmaceutical composition according to the disclosure can be prepared to include a nanostructure of the disclosure, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. By "effective dose" is meant the quantity of a nanostructure according to the disclosure to sufficiently provide measurable SERS signals. Amounts effective for this use will, of course, depend on the tissue and tissue depth, route of delivery and the like.

Typically, dosages used in vitro may provide useful guidance in the amounts useful for administration of the pharmaceutical composition, and animal models may be used to determine effective dosages for specific in vivo techniques. Various considerations are described, e.g., in Langer, Science, 249: 1527, (1990); Gilman et al. (eds.) (1990), each of which is herein incorporated by reference.

As used herein, "administering an effective amount" is intended to include methods of giving or applying a pharmaceutical composition of the disclosure to a subject that allow the composition to perform its intended function.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Supplementary active compounds can also be incorporated into the compositions.

The working examples provided below are to illustrate, not limit, the disclosure. Various parameters of the scientific methods employed in these examples are described in detail below and provide guidance for practicing the disclosure in general.

EXAMPLES

Example 1

Fabrication of Nanocrescent SERS probes. The gold nanocrescent SERS probes are fabricated by rotational deposition of a thin gold layer on polymer nanospheres at certain angles and subsequent dissolution of the sacrificial nanosphere templates. The inner diameter and thickness of nanocrescent SERS probes can be controlled in the fabrication by choosing the size of sacrificial nanosphere templates as well as the gold deposition thickness and angle.

FIG. 2 shows the fabrication procedure, which depict a simple batch nanofabrication method. Glass slides were thoroughly rinsed with deionized water (Millipore, >18 MΩ) and dried under a stream of nitrogen gas. A thin layer of photoresist (Shipley S1818, Shipley, Mass.) was spin-coated on the cleaned glass substrates. Aqueous solutions of polystyrene colloids (300 nm; Duke Scientific, California) were diluted in water to a volume fraction of 0.1%. A monolayer of sacrificial nanospheres was generated by drop-casting the dilute solution of the polystyrene colloids and allowed to dry overnight in a clean zone hood to minimize contamination of the samples by dust, and to stabilize the rate of evaporation. After the arrays of beads dried, a thin gold film was deposited by conventional electron beam evaporation. The sample substrate was placed above the gold source with certain tilt angle (~30°) and the angle can be adjusted ranging from 0° to 45°. Substrate rotates at a constant speed (~60 rpm) during the deposition. The thickness at the bottom of the bowl is measured using TEM to be ~100 nm. The shape of nanocrescent SERS probes depends on the deposition thickness, angle and the size of the nanostructure template (here a nanosphere). The gold coated colloids were released from the glass support into an aqueous suspension by lift-off with acetone in an ultrasonic cleaner (Branson Ultrasonics, CT). Next the gold coated polymer nanospheres were collected by centrifugation (~5000 rpm, 5-10 min.) and are suspended in toluene to dissolve the polymer nanostructure template (here polystyrene). The sample was then centrifuged, and washed 3-4 times in water. The gold nanocrescent SERS probes were collected and resuspended in water or ethanol to form diluted colloids which were subsequently dropped on a 100 μm-thick glass substrate for spectrum measurement.

The structures of the nanocrescent SERS probes maintain their original shape and did not collapse during the process of dissolving the sacrificial nanosphere templates or drying on a surface for imaging. Dispersion of the particles by mild sonication in an ultrasonic cleaner did not deform the nanocrescent SERS probes either. A survey of about 100 gold nanocrescent SERS probes by electron microscopy showed that fewer than 5% of the particles were distorted or broken after the fabrication procedure, including redispersion.

In a specific example, a thin layer of photoresist (Shipley S1818, Shipley, Mass.) was spin-coated on cleaned glass substrates. A monolayer of sacrificial nanospheres was generated by drop-casting a 0.1% solution of polystyrene colloids (150 nm; Duke Scientific, California), which was allowed to dry overnight in a clean-zone hood to minimize contamination of the samples by dust and to stabilize the rate of evaporation. After the arrays of beads dried, metal films in various thicknesses were deposited by conventional electron-beam evaporation. The sample substrate was placed above the metal-pellet sources with a certain tilt angle (~60°) with respect to the substrate surface. The substrate was rotated at a constant speed (~60 revolutions per minute, rpm) during the deposition. The metal-coated colloids were released from the glass support into an aqueous suspension by lift-off with acetone. Next, the coated polymer nanospheres were collected by centrifugation (~5000 rpm, 5-10 min) and suspended in toluene to dissolve the polystyrene. The sample was then centrifuged and washed three to four times in water. The nanocrescents were collected and resuspended in water or ethanol to form diluted colloids.

Fluorescence Imaging and Raman Microspectroscopy. A microscopy system combining fluorescence imaging and Raman spectroscopy was used to monitor the fluorescence intensity and to acquire Raman scattering spectra from single nanocrescents. The system consisted of a Carl Zeiss Axiovert 200 inverted microscope (Carl Zeiss, Germany) equipped with a high-speed, high-sensitivity digital camera (Cascade 512B, Roper Scientific, New Jersey), and a 300 mm focal length monochromator (Acton Research, Massachusetts) with a 1024 pixel×256 pixel cooled spectrograph charge-coupled device (CCD) camera (Roper Scientific, New Jersey). The time-resolved fluorescence images of the nanocrescents were taken using the Cascade camera at a frame rate of 10 frames per second, a 40× objective lens (numerical aperture NA=0.8), a fluorescein isothiocyanate (FITC) fluorescence filter set, and a 100 W mercury lamp for illumination. A 785 nm semiconductor laser was used in the experiments as the excitation source of Raman scattering, and the laser beam was focused by a 100× objective lens on the nanocrescent. The excitation power was measured by a photometer (Newport, Calif.) to be ~1 mW. The Raman scattering light was then collected through the same optical pathway through a long-pass filter and analyzed by the spectrometer.

Analysis of Raman Scattering Spectrum. The nanocrescent SERS probes on a cleaned glass slide are visualized in the dark-field scattering image (FIG. 4a, note no optical filter is used when taking the true color image). A microscopy system combining dark-field scattering imaging and Raman spectroscopy is used to find "hot spots" and acquire Raman scattering spectra of R6G molecules adsorbed on single gold nanocrescent SERS probe. The system consist of a Carl Zeiss Axiovert 200 inverted microscope (Carl Zeiss, Germany) equipped with a darkfield condenser (1.2<NA<1.4), a true-color digital camera (CoolSNAP cf, Roper Scientific, New Jersey), and a 300 mm focal-length monochromator (Acton Research, Massachusetts) with a 1024×256-pixel cooled spectrograph CCD camera with compensation in ultraviolet and near infrared region (Roper Scientific, New Jersey). A 2 μm-wide aperture is placed in front of the entrance slit of the monochromator to keep only single nanostructure (e.g., nanobowl) in the region of interest.

The true-color scattering images of gold nanocrescent SERS probes are taken using a 60× objective lens (NA=0.8) and the true-color camera with a white light illumination by a 100 W halogen lamp. The scattering spectra of gold nanostructure (e.g., nanobowl) are taken in visible light and infrared light region separately, normalized with respect to the spectrum of a non-resonant nanoparticle (i.e. polystyrene) after the subtraction of background, then combined and normalized to unity.

FIG. 4d shows the measured scattering spectra of the three marked nanocrescent SERS probes in FIG. 4a. The spectra are taken in visible light and infrared light region separately, normalized with respect to the spectrum of a non-resonant nanoparticle (i.e. polystyrene) after the subtraction of background, then combined and normalized to unity. Multiple scattering peaks exist for all the nanocrescent SERS probes in the scattering spectra but only nanocrescent SERS probes 1 and 2 have peaks with wavelengths larger than 750 nm. A 785 nm diode laser is used in the experiments as the excitation source, and the laser beam (after attenuating neutral density filter) is focused by the same objective lens on single nanocrescent SERS probes. The laser power delivered on the nanocrescent SERS probe is measured using a photometer (Newport, Calif.) to be ~0.8 mW. The scattering and reflection light is then collected through the same optical pathway as the incident light and then through two 797 nm long-pass Raman filters (optical density >6 below 797 nm and transmission >90% above 800 nm, Omega Filters, VT). The Raman scattering light is resolved by a blaze grating of 300 grooves/mm and imaged by the spectrograph CCD.

In order to make sure that the measured Raman scattering spectrum is from the R6G molecules on a single nanocrescent SERS probes, the laser excited scattering light from gold nanocrescent SERS probes is imaged simultaneously with the white light dark field illumination by a back-illuminated B/W camera (quantum efficiency >95%, Cascade 512B, Roper Scientific, New Jersey). Furthermore a 2 μm-wide aperture is placed in front of the entrance slit of the monochrometer to keep only single nanocrescent SERS probes in the region of interest.

FIG. 4b shows the dark-field scattering image of several nanocrescent SERS probes that are the same as shown in FIG. 4a but the image is taken by the back-illuminated camera and two 797 nm long-pass optical filters are used. Note the laser light is greatly attenuated by the long-pass filters and the halogen illumination light is weak in this wavelength region so they cannot be imaged by ordinary digital cameras if high frame rate needs to be maintained for searching "hot spots". It is interesting to notice in the 3D surface plots of FIGS. 4a and 4b that the relative ratio of overall scattering intensities from three marked nanocrescent SERS probes are different over the whole white light spectrum (FIG. 4a) and in the near infrared light region (FIG. 4b). The relative intensity ratio also corresponds to their scattering spectra. For example, nanocrescent SERS probe 3 has higher overall intensity than nanocrescent SERS probe 2 in the true color image (FIG. 4a), whereas nanocrescent SERS probe 3 disappears and nanocrescent SERS probe 2 stands out in the near infrared image (FIG. 4b). FIG. 4c shows that nanocrescent SERS probe 1 is excited by the laser and the FWHM of the excitation area is ~2 μm.

Analysis of SERS Spectra Using R6G. In this experiment, near infrared laser (785 nm) was used as the excitation source instead of a green laser (514 nm) usually used in other nanosphere-based SERS characterizations where the scattering peak (plasmon resonance) wavelength is usually around 500-600 nm, except the special inter-coupled nanospheres. In addition to the reason of matching the scattering peak wavelength of nanocrescent SERS probes, the near-infrared laser source is more preferable in general bimolecular SERS detection because: (1) it can avoid the excitation of fluorescence from biomolecules; (2) it has a deeper penetration depth in biological tissues; and (3) low photon energy of near infrared laser minimizes photothermal damage to biomolecules and cells. A considerable fluorescence background was not observed, and no "burning" effects were found in the sample area for the used laser power. In addition, the choice of the near-infrared excitation ensures that the SERS effects detected are generated from the sharp edge of the nanocrescent SERS probes, not the few residue nanospheres in our sample, since a near-infrared laser can hardly induce scattering peaks in nanospheres, which are necessary for the effective near-field energy transfer to adsorbed molecules.

Assuming the cross-sectional area of the shown nanocrescent SERS probe is about $1\times10^{-7}$ mm$^2$, there are only $1\times10^{-20}$ mol (~6000) R6G molecules on a nanocrescent SERS probe after the uniform distribution of 1 μL of 1 μM R6G droplet (1 pico mol) on a ~10 mm$^2$ cross-sectional area, that is to say, ~6000 R6G molecules can be detected on a single gold nanocrescent SERS probe; assuming the nanocrescent SERS probe (300 nm inner-diameter and 100 nm bottom-thickness) has an equivalent (slightly smaller) cross-sectional area to a 400 nm diameter nanosphere. The total cross-sectional area is $n\times200^2$ nm$^2$=$1.26\times10^{-7}$ mm$^2$ (~$1\times10^{-7}$ mm$^2$), so the number of R6G molecules staying on the nanostructure (e.g., nanobowl) after drying is about 1 pM×$6.02\times10^{23}$ M$^{-1}$×($1\times10^{-7}$÷10)=6020 (~6000).

According to Nie et al. and Kneipp et al., that the Raman scattering enhancement factor is above $10^{14}$ for the single-molecule single-particle sensitivity, it is estimated the Raman enhancement of a single gold nanostructure (e.g., nanobowl) could be higher than $10^{10}$. As a matter of fact, the enhancement factor could be higher because even fewer molecules are distributed close to the sharp edge area of the nanocrescent SERS probe where most of the enhanced scattering signal is generated.

Though some characteristic peaks in the SERS spectrum of R6G molecules show only moderate enhancement on the nanocrescent SERS probe (FIG. 5b), the area of the "hot spot" of a nanocrescent SERS probe, (the sharp edge), is smaller than that of the nanosphere clusters (their whole surfaces), and thus the actual relative intensity enhancement per unit area should be higher than that shown in the plots. The relative intensity enhancement per unit area on the sharp edge of the nanocrescent SERS probe is estimated larger than $10^3$, considering the nanosphere number (>100) within the laser excitation area. On the other hand, some peaks are not visible on the gold nanospheres but are very distinct on the nanocrescent SERS probes, especially for those vibrational peaks corresponding to aromatic ring bending and stretching, such as 615 cm$^{-1}$, which comes from the aromatic ring in-plane bending. In this case, the relative enhancement of the sharp edge compared to nanosphere clusters could be larger than 105. The total cross sectional area of 100 60 nm nanospheres is 100× π×60$^2$ nm$^2$=$1.13\times10^{-6}$ mm$^2$. As a conservative assumption, the cross sectional area of the sharp edge is smaller than 1% of the whole nanostructure (e.g., nanobowl), that is, $1\times10^{-7}$ mm$^2$÷100=$1\times10^{-9}$ mm$^2$, so the relative Raman peak intensity per unit area on the sharp edge of a gold nanostructure (e.g., nanobowl) can be 1000 times higher than that of 100 60 nm nanosphere if the total Raman peak intensities from both the single nanostructure (e.g., nanobowl) and nanosphere clusters are equivalent. The peak intensity at 615 cm$^{-1}$ on the nanostructure (e.g., nanobowl) is at least 100 times larger than that on the nanospheres, so a relative enhancement factor of above $10^5$ can be obtained.

The Raman enhancement factor of an on-resonance Au nanosphere has been reported to be $10^3$-$10^4$ using 514 nm laser excitation. This enhancement factor is much smaller than that obtained from our single on-resonance nanoscrescent moon, which is also supported by the simulation results presented here. Due to the interparticle plasmon coupling, the plasmon resonance wavelength of a cluster of Au nanospheres could shift to the range of near-infrared light and the nanospheres can be on-resonance using an NIR laser excitation. As reported before, an 830 nm laser excitation source was used and a Raman enhancement factor of ~$10^9$ was obtained. However, because of the random pattern of nanoparticle aggregations, the Raman enhancement factors are very different from place to place on an Au nanosphere cluster. A strong Raman enhancement could be obtained from particular positions on an Au nanosphere cluster after many trials in an unpredictable way. In contract, the plasmon resonance of the nanocrescent SERS probe is controllable and predictable because it is designed and fabricated as such. On the other hand, the Raman enhancement effect of a single nanocrescent SERS probe does not depend on the coupling between multiple particles, which makes the single nanocrescent SERS probe an individual SERS substrate.

To calculate the field enhancement factor, the 2-D Helholtz equation was solved using finite element method. The computation nanocrescent SERS probes are round with a radius of 0.25 nm to avoid computational anomalies. The wavelength-dependent refractive index of the nanostructures is set to the values of built gold reported by Johnson and Christy. It was also assumed that the nanocrescent SERS probes are in water in accordance with the experiments. As shown in FIG. 3, the incident wave is polarized transverse magnetic with respect to the nanocrescent SERS probe. The effect of retardation is fully realized in the simulations. The enhancement factor is determined for the amplitude ratio between the calculated nanocrescent SERS probe near-field and the incident field. The sharp edge area (two sharp tips in the two-dimensional simulation) exhibits the highest level of field enhancement as expected. At this wavelength, of maximum field enhancement, the enhancement factor reaches ~$10^2$. Since the Raman enhancement factor is proportional to the fourth power of the field amplitude enhancement 12, the Raman enhancement factor of single gold nanocrescent SERS probe could be up to $10^{11}$ at the shown resonant wavelength. While the nanocrescent SERS probe shows scattering peak within the wavelength region from 700 nm to 900 nm, no scattering peaks are found in the simulation for a nanosphere in the similar size within this wavelength region.

R6G molecules (about 6,000 molecules) were detected on a single gold nanostructure (e.g., nanobowl) through the near infrared laser induced SERS spectroscopy, and the estimated Raman enhancement factor is larger than $10^{10}$. Based on the observed results, the sharp-edge gold nanocrescent SERS probes promise potential uses in ultrasensitive Raman, biomolecules and cellular imaging, and molecular medicine.

The nanocrescent SERS probes redistributed on a cleaned glass slide are visualized in the dark-field scattering image (FIG. 4a, note no optical filter is used when taking the true color image). FIG. 4d shows the measured scattering spectra of the three marked nanocrescent SERS probes in FIG. 4a. Multiple scattering peaks exist for all the nanocrescent SERS probes in the scattering spectra, but only nanocrescent SERS probes 1 and 2 have peaks with wavelengths larger than 750 nm. FIG. 4b shows the dark-field scattering image of the same nanostructure (e.g., nanobowl) as shown in FIG. 4a, but the image is taken by a back-illuminated B/W camera (quantum efficiency >95%, Cascade 512B, Roper Scientific, New Jersey), and two 797 nm long-pass optical filters (Omega Filters, VT) are used. It is interesting to notice in the 3D surface plots of FIGS. 4a and 4b that the relative ratio of scattering intensities from three marked nanostructure (e.g., nanobowl) are different over the whole white light spectrum (FIG. 4a) and in the near infrared light region (FIG. 4b). The relative intensity ratio also corresponds to their scattering spectra in FIG. 4d. For example, nanocrescent SERS probe 3 has higher overall intensity than nanostructure (e.g., nanobowl) 2 in the true color image (FIG. 4a), whereas nanostructure (e.g., nanobowl) 3 disappears and nanocrescent SERS probe 2 stands out in the near infrared image (FIG. 4b).

The simulation results indicate that the common scattering peak near 500 nm is clearly originated from the multipolar excitation of surface plasmon resonance around the outer periphery. Considering the high intensity of the electric fields concentrated at and near the edges, it is appropriate to attribute the peaks to the local plasmon resonances in the edge area and their interplay. It is worth noting that the local field enhancement near the sharp edges of nanocrescent moons greatly exceeds the enhancement originated from the same edges with no cylindrical cavity behind them.

The 785 nm laser excitation light scattered from a single gold nanocrescent SERS probe is imaged simultaneously with the scattering light from the white light dark-field illumination by the back-illuminated B/W camera, in order to make sure that the measured Raman scattering spectrum is from the R6G molecules on a single nanocrescent SERS probe. FIG. 4c shows that nanocrescent SERS probe 1 is excited by the laser and the FWHM (full width at half max) of the excitation area is ~2 μm. The white-light illumination is only kept on when searching the nanostructure (e.g., nanobowl) and it is turned off during Raman spectra acquisition. The laser power delivered on the nanocrescent SERS probe is measured using a photometer (Newport, Calif.) to be ~0.8 mW.

Figure 5A:
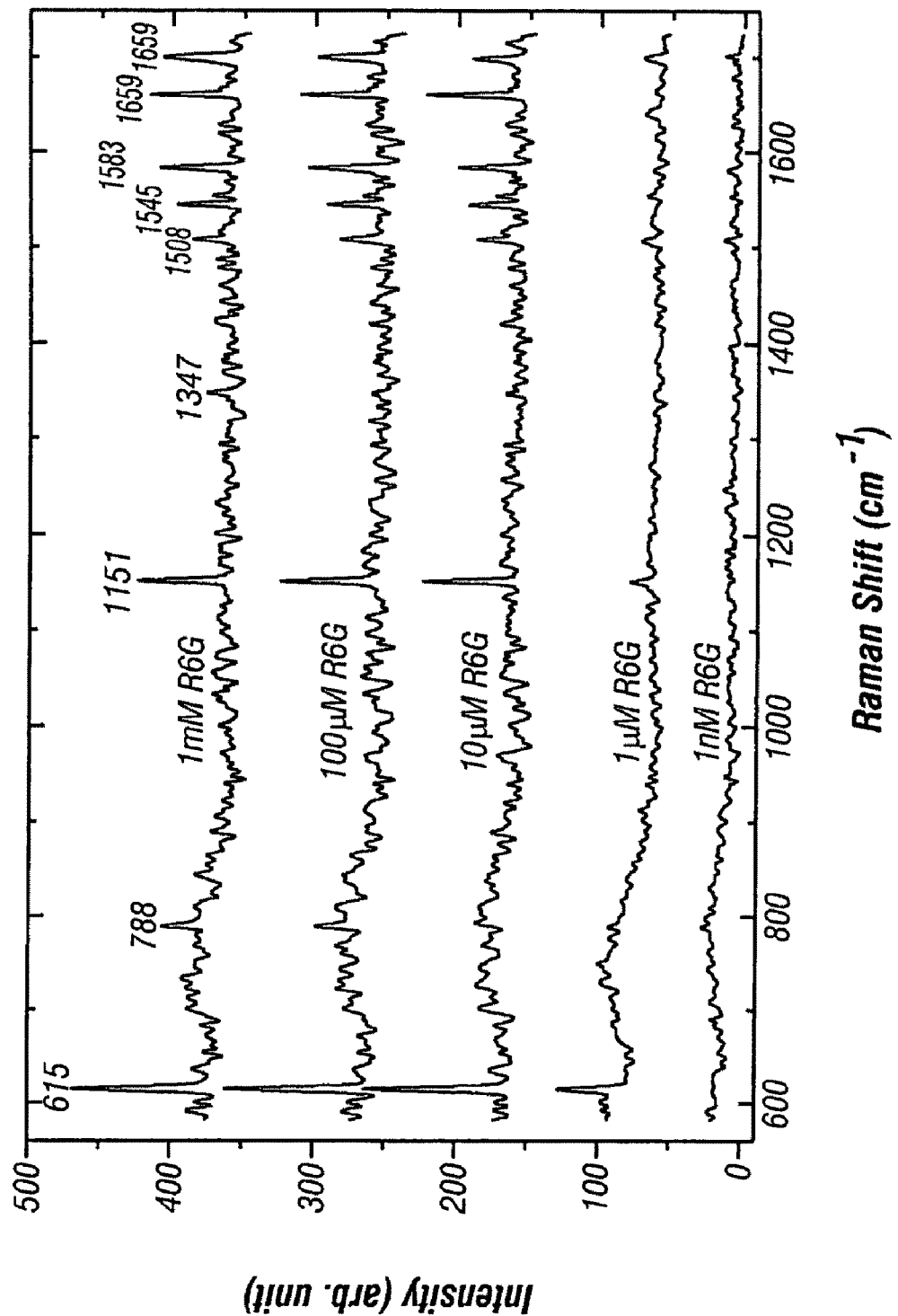
FIGS. 5A-B shows SERS spectra of R6G molecules. (a) SERS spectra of different concentrations of R6G molecules adsorbed on a single nanocrescent SERS probe SERS "hot spot". Minor base line singles are corrected for all shown spectra. (b) SERS spectra of 1 mM R6G molecules on a single gold nanocrescent SERS probe and 60 nm colloidal nanospheres.
Figure 5B:
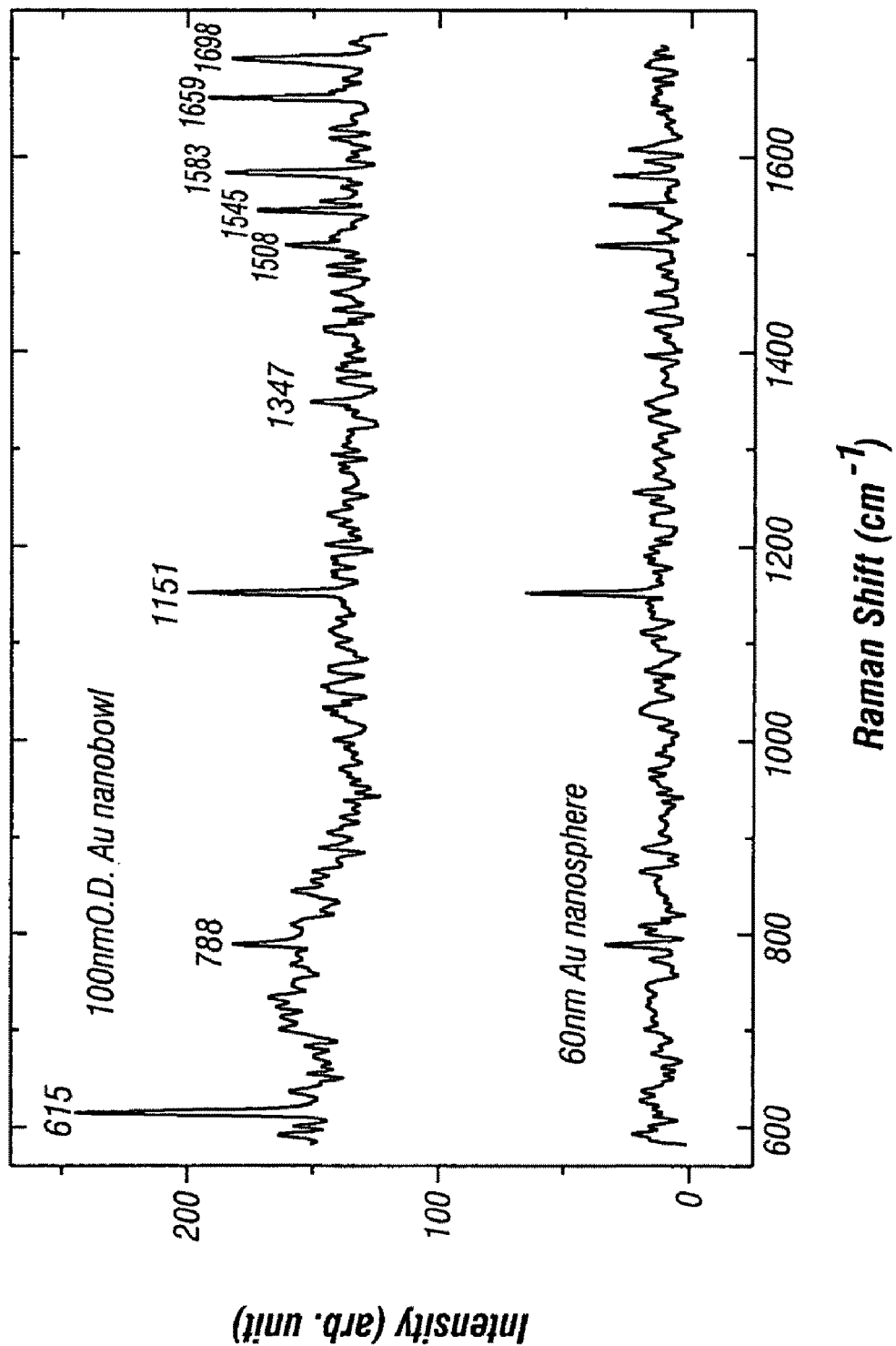

Different concentrations of R6G molecules were tested on the same nanocrescent SERS probes in the following way: first, the position was marked where the imaged nanostructure (e.g., nanobowl) are on the glass substrate. A 1 μL droplet of 1 nM R6G is then spread on the marked position over an area of about 10 mm². With the 785 nm laser excitation, the SERS spectra on the chosen single gold nanocrescent SERS probes are taken with a 10-second exposure time and averaged over 5 recordings. At this concentration level, no apparent Raman peaks are visible for over 30 examined nanocrescent SERS probes. Then, a 1 μL droplet of 1 μM R6G is placed on the same marked position as before. The same nanocrescent SERS probes examined previously are found under the dark-field microscopy and the SERS spectra on those gold nanocrescent SERS probes are taken again. The Raman peaks are barely seen at this concentration level on some nanocrescent SERS probes. The same procedures with different concentrations are repeated on each of those nanocrescent SERS probes. The SERS spectra of different concentrations of R6G molecules from one of nanocrescent SERS probe "hot spots" are shown in FIG. 5a after baseline corrections. Each Raman spectrum measurement is done under the same acquisition conditions. The peak intensities increase with the concentration of the added R6G droplets and almost saturate after the addition of 100 μM R6G droplet. Characteristic peaks are not found in the spectra taken from the areas without nanocrescent SERS probes for all the concentrations. For the purpose of comparison, ~1 nM 60 nm gold nanospheres (Ted Pella, Inc., Redding, Calif.) are cast on a glass slide to form clusters, and 1 mM R6G molecules adsorbed on the nanosphere cluster are detected using the same procedures. No "hot spots" as good as the shown nanocrescent SERS probes are found for over 30 examined spots on the nanosphere clusters. FIG. 5b shows the comparative Raman spectra of 1 mM R6G on a gold nanostructure (e.g., nanobowl) and 60 nm gold nanosphere clusters. The R6G Raman spectra from the gold nanostructure (e.g., nanobowl) contains some peaks with comparatively higher intensities than those in the spectra from the nanosphere clusters, and also contains some peaks that are not visible in the spectra from the nanosphere clusters.

Some nanocrescent SERS probes exhibit different scatter spectra and colors as shown in FIG. 4, which is possibly due to the slight difference in the geometrics and orientations with respect to the incident light. Since the local field enhancement factor is also related to the orientation of the reduced-symmetry gold nanocrescent SERS probes with respect to the incident field, it could be higher at special orientations.

Example 2

Figure 9B:
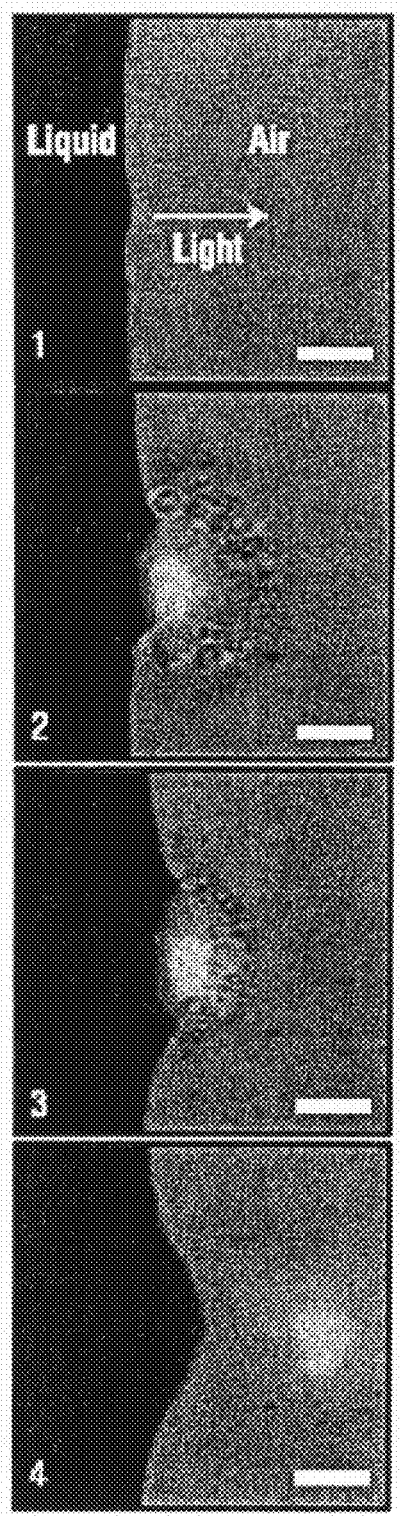

In addition, the invention examines the ability of the nanostructures of the invention and related structures to include micro- and nano-fluidic movement. In an experiment to support this mechanism, a 2 μl water drop is dispensed on a hydrophobic glass slide, and a focused 785 nm laser beam with tunable power is used as the illumination source. The contact angle of the water drop on the glass slide was approximately 60° (other angles can be utilized). Approximately 1 nM PNPs were present in the liquid. When a 20 mW, 785 nm focused light spot was illuminated on the liquid contact line and translated outwards, the liquid evaporation, droplet formation and contact-line advance are clearly visible (FIG. 9b). The optically controlled advance of the liquid-air interface follows the light translation and stops on the removal of the illumination. However, as the liquid is unconfined in this case, the liquid flow cannot be guided unidirectionally and thus the flow speed is low.

Figure 9C:
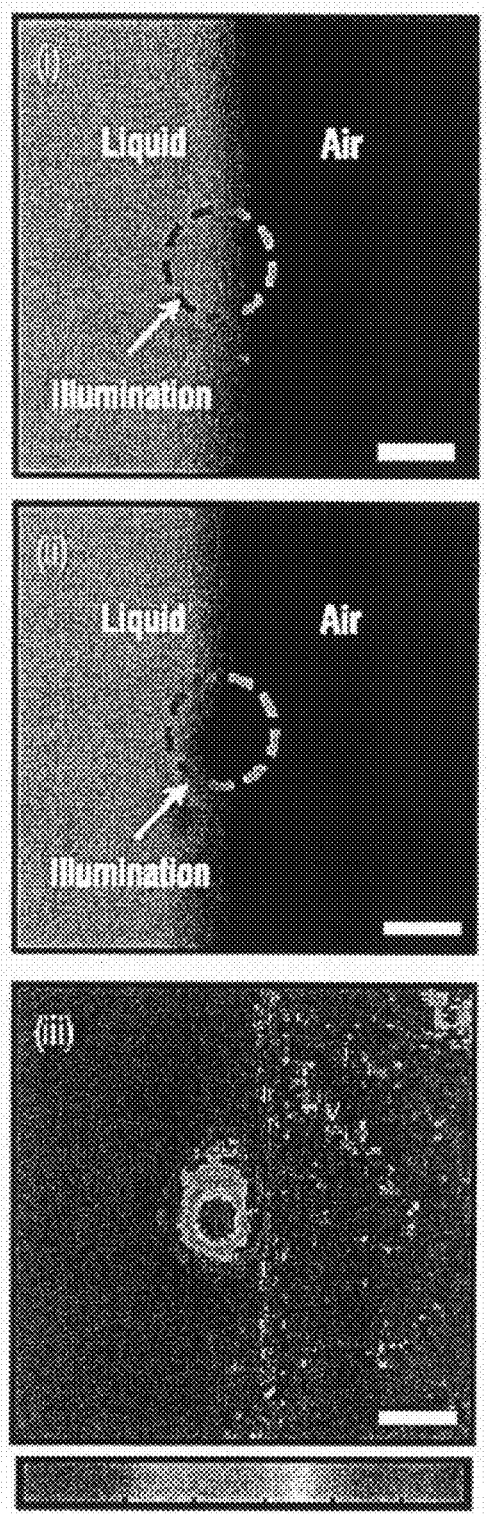

In order to characterize the temperature distribution of the PNP-suspended liquid with a high spatial resolution, the thermal fluorescence quenching was measured by fluorescence microscopy. As shown in FIG. 9c, a water solution containing 100 μM fluorescein, 1 M N-2-hydroxyethylpiperazine-N'-2'-ethanesulphonicacid (HEPES) buffer and 1 nM PNPs were illuminated by a 20 mW, 785 nm focused laser spot near the liquid-air interface for 1 s. The fluorescence intensity at the illuminated area decreased markedly owing to the localized increase in liquid temperature. The temperature distribution was then calculated according to the previously established relations between temperature and fluorescence intensity change (see FIG. 15). Most of the liquid body remains at room temperature (22° C.) except for the illuminated circular area with a ~10 μm diameter where the temperature shows a Gaussian distribution and the highest temperature is close to 60° C. (lower than 100° C. owing to the energy loss in fluorescence thermal quenching). Another experiment using thermochromic microcapsules in the liquid also showed that the temperature of the liquid remains lower than 40° C. even at positions as close as 10 μm from the illuminated area where the water is boiling (see FIG. 16).

Figure 10B:
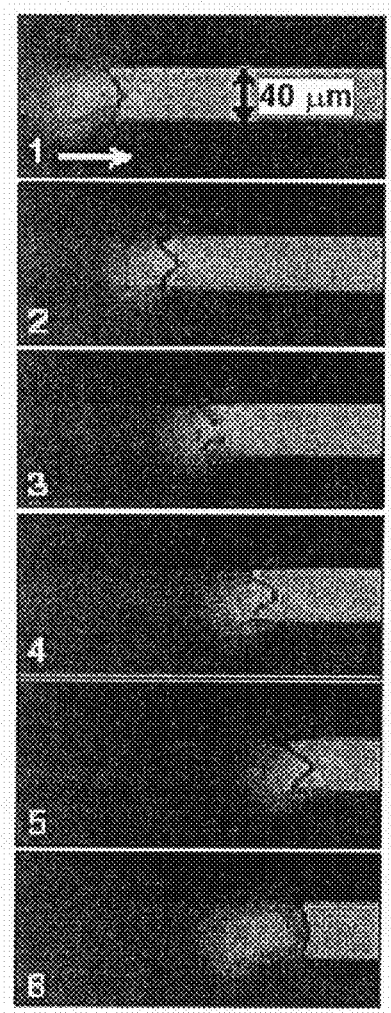
Figure 10C:
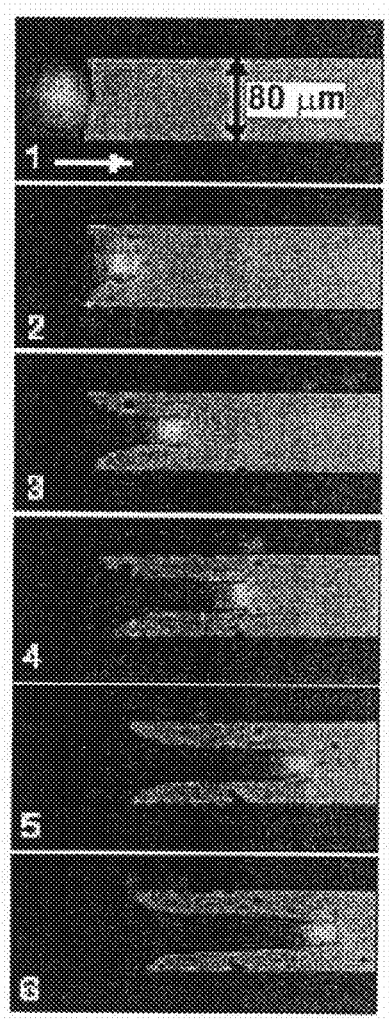

FIG. 10b shows that the 0.5 nM PNP suspended 1×PBS buffer in a 40-μm-wide, 5-μm-high channel was driven and guided by the translation of a focused 10 mW, 785 nm laser spot at a speed of ~50 μm s$^{-1}$. For a channel width (80 μm) much larger than the focused light spot (10 μm), the optofluidic flow can also be realized. An extruding liquid flow is generated as only a portion of the liquid-air interface is illuminated by the light spot (FIG. 10c).

Figure 10D:
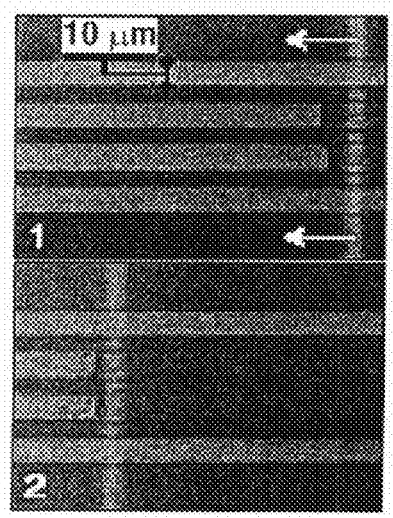
Figure 10E:
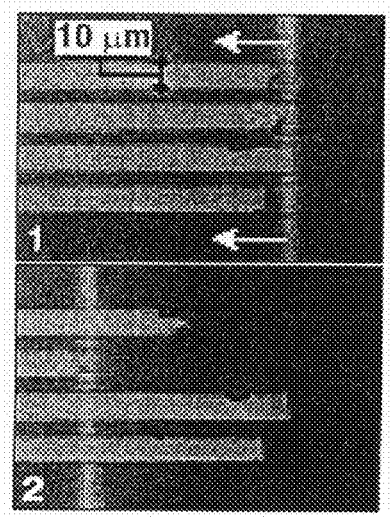

With PNPs, the liquid flow in parallel 10-μm-wide microfluidic channels can be driven and guided simultaneously by a focused laser line at the speed of ~10 μm s$^{-1}$ as shown in FIG. 10d. It is worth noting that the light power illuminated on each channel is smaller than 1 mW. Pure water and 60-nm gold colloidal nanoparticles with an absorption band unmatched to the laser wavelength were introduced as the controls (FIG. 10e) in two parallel channels. They show no water evaporation, no droplet formation and thus no response to the optofluidic control. As a side-by-side comparison, PNP-activated optofluidic flows in the adjacent two parallel channels were observed. The maximal optofluidic flow speeds in these two channels are different because the introduced liquids have different PNP concentrations.

Among the involved physical mechanisms, the rate of droplet formation, growth and coalescence provides an overall optofluidic flow speed of ~1 mm s$^{-1}$.

The light illumination power, microchannel dimension and PNP concentration are three major tunable factors to determine the rate of droplet formation and coalescence, thus characterizing the optofluidic flow speed. FIG. 11a shows the speed of the optofluidic flow versus the power of light illumination for 1 nM PNP solutions and FIG. 11b shows the maximal flow speed versus the PNP concentration for 20-mW illumination power.

The characterizations were carried out for three different channel widths: 10, 40 and 80 μm. An optofluidic flow speed in the 10 μm channel can be as high as 500 μm s- using the 20 mW light power. The flow speed can be further increased by adopting narrower microchannels, more accurate light control and PNPs with higher photothermal efficiency.

In addition to individual straight channels, a functional microfluidic circuit often consists of channel junctions. The positioning of liquid flow at channel junctions requires complicated valve systems. The invention overcomes the complicated valve channels using optofluidic control with superior directionality at the channel junctions without any valve or pump. In the two adjacent T-shaped junctions, 1 nM PNP water solution is introduced from the right branch channel (FIG. 12a). All channels with the same width (40 μm) are open to the atmosphere and no previous surface patterning was performed; all the channels therefore have an equal chance to be filled with pressure-driven flow. In three experimental trials, the liquid was optically driven and guided into three different branches without filling other branches as shown in FIG. 12b. The optofluidic flow speed remains almost the same after the liquid enters the chosen branch, even with sharp turns, because most of the PNPs near the liquid-air interface will follow the direction of the guiding light and be drawn to the advancing liquid-air interface.

Preparation of photothermal nanoparticles (PNP). The PNP, gold nanocrescents were prepared as described above: first, 100 nm polystyrene nanoparticles (Duke Scientific, California) are dispersed on a silicon wafer with a thin film of chromium coating; second, a thin layer (15~20 nm) of gold was deposited on the polystyrene nanoparticles from an oblique angle (~60° respect to the wafer surface) when the wafer is rotating at a speed of ~60 RPM; third, the polystyrene nanoparticles with gold nanocrescent shell were lifted off from the wafer by sonication and collected in water suspensions; the PNP suspension was subjected to washing at ~300 RPM centrifugation and 0.4 μm-nanopore filtering to remove impurities. The PNP concentration can be controlled by the number of polystyrene nanoparticles (concentration provided by the vendor) dispersed on the wafer and the final suspension volume. Using the technique above ~1 nM, or ~10$^{14}$ particles/L, PNP suspension was produced as a stock solution.

Figure 15:
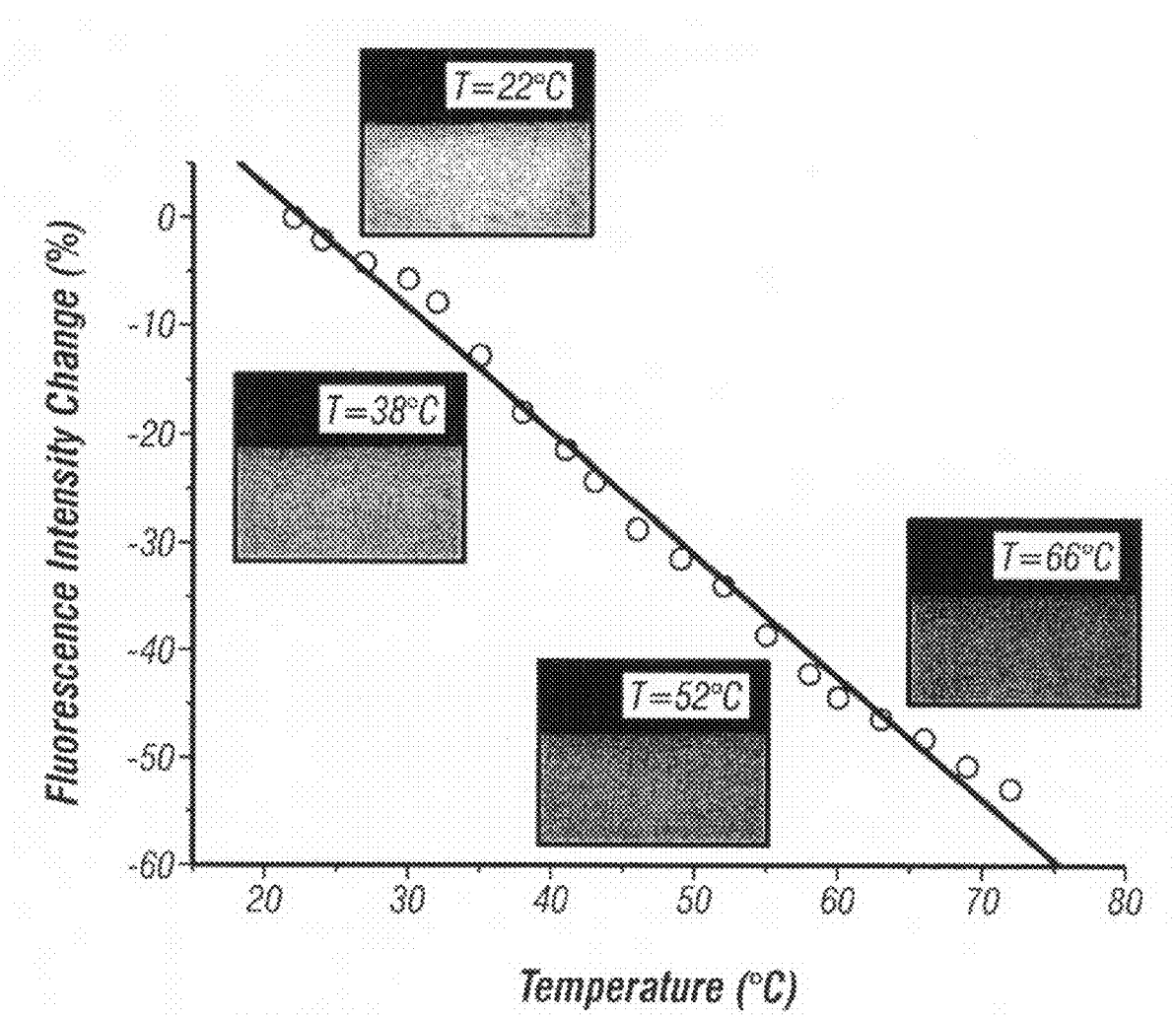
FIG. 15 shows the fluorescence intensity change vs. liquid temperature. The insets show the fluorescence intensity images of the same liquid at 22, 38, 52, and 66° C., respectively during the heating process.

Calibration of temperature vs. fluorescence intensity. The thermally-induced fluorescence intensity decrease vs. temperature increase was characterized by heating the liquid containing 100 μM fluorescein, 1 M N-2-Hydroxyethylpiperazine-N'-2'-ethanesulfonic acid (HEPES) buffer, and 1 nM photothermal nanoparticles using an electric resistor heater and temperature measuring with a thermal couple. The liquid was enclosed in a millimeter scale transparent chamber to minimize evaporation during the heating, because the water evaporation will cause the increase of fluorophore concentration and fluorescence intensity. The liquid was heated from room temperature (22° C.) to ~70° C., and the fluorescence intensity decreased (FIG. 15). The mercury lamp illumination was turned on only when the fluorescence images were being taken, which minimized the effect of photobleaching in the measurement.

Figure 16A:
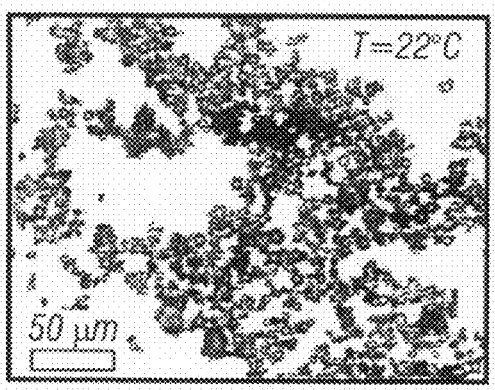
FIG. 16A-D shows the thermochromic microcapsule temperature indicators in thermal heating and PNP-activated photothermal heating. A) Color image of thermochromic microcapsules at 22° C. B) Color image of the same microcapsules at 40° C. after thermal heating. C) Color image of thermochromic microcapsules in 1 nM PNP suspensions. D) Color image of the same microcapsules when a 10 mW 785 nm focused laser spot is illuminated on the liquid-air interface and the PNP cause liquid boiling and droplet forming.
Figure 16B:
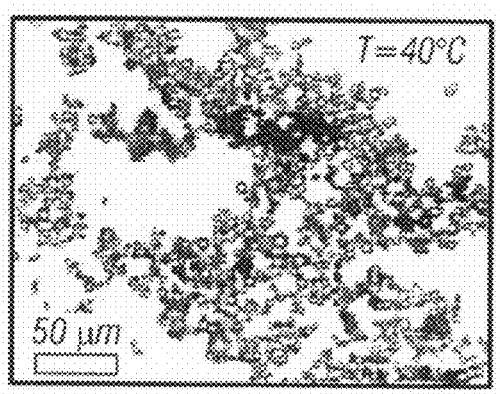
Figure 16C:
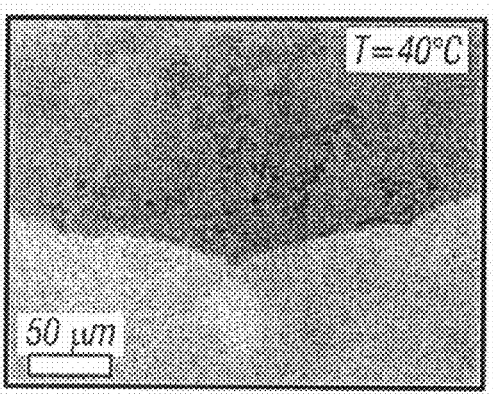
Figure 16D:
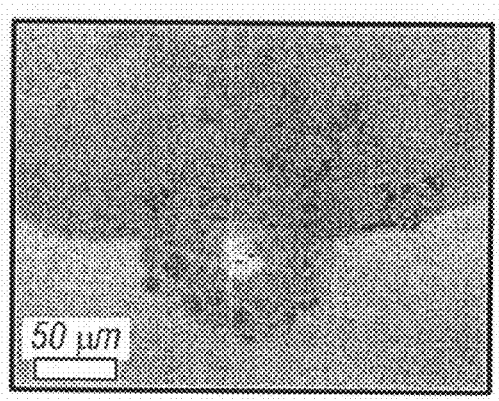

Thermochromic microcapsule temperature indicator. Three kinds of thermochromic microcapsules were kindly provided by Kelly Chemical Corporation (Taiwan). Among them there are light yellow, magenta and dark blue microcapsules, that become colorless when temperature is higher than 30, 40 and 70° C., respectively. These capsules were mixed together in water and in 1 nM PNP suspension, respectively. For the sample of thermochromic microcapsules in water, an electric resistor heater was used to increase the temperature and a thermal couple to measure the temperature (FIGS. 16a, b). Due to the low color contrast of the light yellow microcapsules, their color change was difficult to detect. The magenta microcapsules become colorless when the temperature rises to 40° C. while the dark blue microcapsules remain the same color as expected. For the sample of thermochromic microcapsules in PNP suspension, a 10 mW 785 nm focused laser spot was used to illuminate the liquid-air interface. Nearly all the magenta and dark blue thermochromic microcapsules remain the same color while water is boiling at the liquid-air interface even when they are a few microns away from the laser spot (FIGS. 16c, d).

Figure 17:
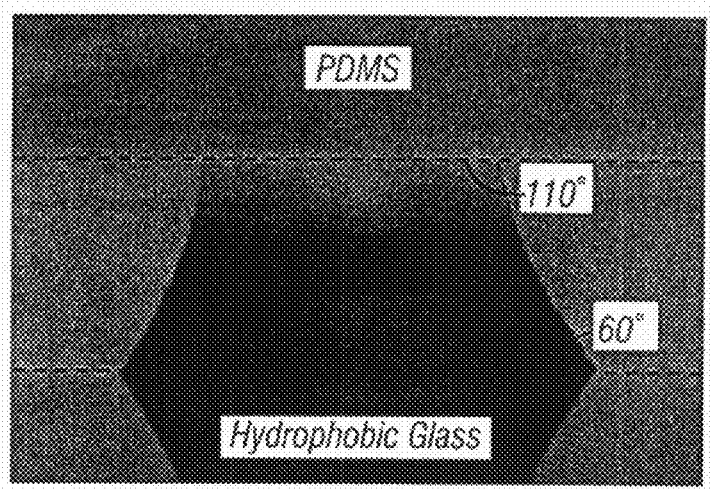
FIG. 17 shows liquid contact angles on hydrophobic glass and PDMS surface. A water drop is sandwiched by a PDMS slab (top) and a hydrophobic glass slide (bottom) on which the contact angles are 110° and 60°, respectively. Due to the high reflectivity of glass, the reflection image of the water drop can be seen.

Preparation of hydrophobic glass slides and PDMS microfluidic chips. The hydrophobic glass slides were prepared as follows. The precleaned 1 mm-thick glass slides (Fisher Scientific, PA) were incubated in Hexamtheyldisilazane (HMDS) vapor deposition chamber for 10 minutes to form a hydrophobic HMDS monolayer on the glass surface. The glass slides were also subject to acetone and isopropanol wash to remove dust before immediate use. The PDMS microfluidic chip was made based on the following procedure: a replication mold consisting of 5 μm-high ridges was photolithographically patterned on a silicon wafer using SU-8 2005 negative-tone photoresist (MicroChem Corp., Massachusetts); the 10:1 mixture of PDMS monomer and curing agent (Dow Corning) was cast on the SU-8 mold to become a 500 μm-thick film which was cured in a 90° C. oven for 10 minutes; after the PDMS film was completely solidified, it was peeled off from the mold and recessed grooves in the same pattern as the mold are generated on PDMS surface. PDMS slabs with groove patterns are cut from the film using razor blade, and can be directly placed on the hydrophobic glass to form microfluidic devices that were used in the experiments. Since the microchannel is an enclosed structure, it is difficult to measure liquid contact angles. The angles were measured using the contact angles of a water droplet sandwiched by a PDMS slab and a hydrophobic glass slide (FIG. 17). A liquid contact angle measurement system (Kruss USA, California) was used to acquire the side-view image and calculate the contact angles.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A nanostructure comprising a geometric shell having an opening defined by a sharp edge, wherein the nanostructure has a cross-section diameter of about 100 nm to about 300 nm and wherein the nanostructure undergoes Surface enhanced Raman scattering (SERS) when contacted with electromagnetic radiation at near infrared wavelengths.

2. The nanostructure of claim 1, wherein the nanostructure comprises one or more noble metals, or one or more noble metals and at least one magnetic metal.

3. The nanostructure of claim 2, wherein the nanostructure comprises a functional group linked to a noble metal of the nanostructure.

4. The nanostructure of claim 1, wherein the nanostructure comprises one or more noble metals, or one or more noble metals and at least one magnetic metal.

5. The nanostructure of claim 1, wherein the nanostructure has an inner radius r and an outer radius R, wherein said outer radius R is greater than the inner radius r, and wherein the nanostructure has a greatest thickness opposite the opening, and wherein the edge has a thickness that is less than the greatest thickness.

6. The nanostructure of claim 1 in a pharmaceutically acceptable carrier.

7. A nanostructure of claim 1, comprising a functional group that associates with a target analyte.

8. The nanostructure of claim 7, wherein the functional group comprises a surface bound reversibly-binding receptor, the receptor specific for the target analyte.

9. The nanostructure of claim 7, wherein the nanostructure further comprises a self-assembled monolayer formed on the surface of the nanostructure.

10. A method for detection of a target analyte, comprising:
a) providing a plurality of nanostructures of claim 7;
b) a device that measures surface enhanced Raman spectroscopy (SERS) detection;
c) contacting the plurality of nanostructures with a fluid suspected of or having the target analyte;
d) contacting the fluid with an electromagnetic radiation at a desired wavelength sufficient to cause SERS; and
e) detecting SERS from the plurality of nanostructures using the device.

11. A microfluidic system comprising:
one or more microfluidic channels;
a fluid;
a plurality of nanostructures as set forth in claim 1, wherein the plurality of nanostructures are dispersed in the fluid; and
means for contacting the leading edge of the fluid in the microchannel with electromagnetic radiation sufficient to induces surface enhanced Raman scattering (SERS), wherein the SERS moves the fluid through the microchannel.

12. A metallic nanostructure comprising a spherical, asymmetrical tapered metallic shell having a single round opening surrounded by an edge, wherein the nanostructure has an inner radius r and an outer radius R, wherein said outer radius R is greater than the inner radius r, and wherein the nanostructure has a greatest thickness opposite the opening, and wherein the edge has a thickness that is less than the greatest thickness and wherein the nanostructure has a cross-section diameter of about 100 nm to about 300 nm.

13. The metallic nanostructure of claim 12, further comprising two or more layers of different metals.

14. The metallic nanostructure of claim 12, further comprising functional groups attached thereto.

15. The metallic nanostructure of claim 12, having magnetic properties.

16. A method for making a nanostructure comprising:
a) dispersing template nanostructures on a surface;
b) depositing one or more metal materials onto the template nanostructure to form coated nanostructures; and
c) removing the coated nanostructures from the surface, wherein the surface of the template nanostructure as it approaches the surface comprises less metal material than any other part of the template nanostructure and wherein the area of the template nanostructure in contact with the surface is free of a metal material.

17. The method of claim 16, further comprising decomposing the template nanostructure.

18. The method of claim 16, further comprising rotating the surface while depositing the one or more metal materials on the template nanostructure.

19. The method of claim 16, wherein the template nanostructure comprises a nanosphere.

* * * * *